United States Patent
Jani et al.

(10) Patent No.: US 9,268,909 B2
(45) Date of Patent: Feb. 23, 2016

(54) APPARATUS, SYSTEM, AND METHOD TO ADAPTIVELY OPTIMIZE POWER DISSIPATION AND BROADCAST POWER IN A POWER SOURCE FOR A COMMUNICATION DEVICE

(71) Applicant: Proteus Digital Health, Inc., Redwood City, CA (US)

(72) Inventors: Nilay Jani, San Jose, CA (US); Douglas Webb, Los Altos, CA (US); Jonathan Withrington, San Francisco, CA (US); Jeffrey Berkman, Saratoga, CA (US); Haifeng Li, Sunnyvale, CA (US)

(73) Assignee: Proteus Digital Health, Inc., Redwood City, CA (US)

( * ) Notice: Subject to any disclaimer, the term of this patent is extended or adjusted under 35 U.S.C. 154(b) by 0 days.

(21) Appl. No.: 14/435,240

(22) PCT Filed: Oct. 15, 2013

(86) PCT No.: PCT/US2013/065041
§ 371 (c)(1),
(2) Date: Apr. 13, 2015

(87) PCT Pub. No.: WO2014/062674
PCT Pub. Date: Apr. 24, 2014

(65) Prior Publication Data
US 2015/0294077 A1    Oct. 15, 2015

Related U.S. Application Data

(60) Provisional application No. 61/715,610, filed on Oct. 18, 2012.

(51) Int. Cl.
*H04B 1/04*    (2006.01)
*G06F 19/00*    (2011.01)
(Continued)

(52) U.S. Cl.
CPC ........ *G06F 19/3412* (2013.01); *G06F 19/3462* (2013.01); *H04B 17/21* (2015.01); *H04B 1/1607* (2013.01); *H04N 21/4436* (2013.01)

(58) Field of Classification Search
CPC .. H03G 3/004; H02J 2007/005; H02J 7/0047; H05K 5/0086; Y10T 307/406
USPC ........ 455/343.1, 343.2, 343.5, 571, 572, 574, 455/127.1; 320/107, 112, 134, 149, 114, 320/162
See application file for complete search history.

(56) References Cited

U.S. PATENT DOCUMENTS

| | | |
|---|---|---|
| 1,548,459 A | 8/1925 | Hammer |
| 3,589,943 A | 6/1971 | Grubb et al. |

(Continued)

FOREIGN PATENT DOCUMENTS

| | | |
|---|---|---|
| CN | 1588649 | 3/2005 |
| DE | 10313005 | 10/2004 |

(Continued)

OTHER PUBLICATIONS

AADE, "AADE 37th Annual Meeting San Antonio Aug. 4-7, 2010" American Association of Diabetes Educators (2010); http://www.diabeteseducator.org/annualmeeting/2010/index.html; 2 pp.

(Continued)

*Primary Examiner* — Sonny Trinh
(74) *Attorney, Agent, or Firm* — K&L Gates LLP

(57) ABSTRACT

Provided is an apparatus, system, and method for stabilizing battery voltage of a battery device while optimizing power delivered to a receiver during communication of a broadcast packet. A logic circuit is configured to receive a broadcast packet having a predetermined number of bits for communication by a controller to a receiver located remotely from the controller, determine a number of cycles in which a sampled battery voltage is either greater than or less than or equal to a nominal battery voltage over a first subset of the predetermined number of bits of the broadcast packet and performs either a tune-up or a tune-down procedure based on the number of cycles counted in which the sampled battery voltage is not equal to the nominal battery voltage for more than one half of a total number of cycles counted.

20 Claims, 6 Drawing Sheets

(51) Int. Cl.
*H04B 17/21* (2015.01)
*H04N 21/443* (2011.01)
*H04B 1/16* (2006.01)

(56) References Cited

U.S. PATENT DOCUMENTS

| | | | |
|---|---|---|---|
| 3,607,788 A | 9/1971 | Adolph | |
| 3,642,008 A | 2/1972 | Bolduc | |
| 3,679,480 A | 7/1972 | Brown et al. | |
| 3,682,160 A | 8/1972 | Murata | |
| 3,719,183 A | 3/1973 | Schwartz | |
| 3,799,802 A | 3/1974 | Schneble, Jr. et al. | |
| 3,828,766 A | 8/1974 | Krasnow | |
| 3,837,339 A | 9/1974 | Aisenberg et al. | |
| 3,849,041 A | 11/1974 | Knapp | |
| 3,893,111 A | 7/1975 | Cotter | |
| 3,944,064 A | 3/1976 | Bashaw et al. | |
| 3,967,202 A | 6/1976 | Batz | |
| 3,989,050 A | 11/1976 | Buchalter | |
| 4,017,856 A | 4/1977 | Wiegand | |
| 4,055,178 A | 10/1977 | Harrigan | |
| 4,062,750 A | 12/1977 | Butler | |
| 4,077,397 A | 3/1978 | Ellis | |
| 4,077,398 A | 3/1978 | Ellis | |
| 4,082,087 A | 4/1978 | Howson | |
| 4,090,752 A | 5/1978 | Long | |
| 4,106,348 A | 8/1978 | Auphan | |
| 4,129,125 A | 12/1978 | Lester | |
| 4,166,453 A | 9/1979 | McClelland | |
| 4,239,046 A | 12/1980 | Ong | |
| 4,251,795 A | 2/1981 | Shibasaki et al. | |
| 4,269,189 A | 5/1981 | Abraham | |
| 4,331,654 A | 5/1982 | Morris | |
| 4,345,588 A | 8/1982 | Widder et al. | |
| 4,418,697 A | 12/1983 | Tama | |
| 4,425,117 A | 1/1984 | Hugemann | |
| 4,439,196 A | 3/1984 | Higuchi | |
| 4,494,950 A | 1/1985 | Fischell | |
| 4,559,950 A | 12/1985 | Vaughan | |
| 4,564,363 A | 1/1986 | Bagnall et al. | |
| 4,635,641 A | 1/1987 | Hoffman | |
| 4,654,165 A | 3/1987 | Eisenber | |
| 4,663,250 A | 5/1987 | Ong et al. | |
| 4,669,479 A | 6/1987 | Dunseath | |
| 4,687,660 A | 8/1987 | Baker et al. | |
| 4,725,997 A | 2/1988 | Urquhart et al. | |
| 4,749,575 A | 6/1988 | Rotman et al. | |
| 4,763,659 A | 8/1988 | Dunseath | |
| 4,767,627 A | 8/1988 | Caldwell et al. | |
| 4,784,162 A | 11/1988 | Ricks | |
| 4,793,825 A | 12/1988 | Benjamin et al. | |
| 4,844,076 A | 7/1989 | Lesho | |
| 4,876,093 A | 10/1989 | Theeuwes et al. | |
| 4,896,261 A | 1/1990 | Nolan | |
| 4,975,230 A | 12/1990 | Pinkhasov | |
| 4,987,897 A | 1/1991 | Funke | |
| 5,000,957 A | 3/1991 | Eckenhoff et al. | |
| 5,016,634 A | 5/1991 | Vock et al. | |
| 5,018,335 A | 5/1991 | Yamamoto et al. | |
| 5,079,006 A | 1/1992 | Urguhart | |
| 5,110,441 A | 5/1992 | Kinlen et al. | |
| 5,160,885 A | 11/1992 | Hannam et al. | |
| 5,167,626 A | 12/1992 | Casper | |
| 5,176,626 A | 1/1993 | Soehendra | |
| 5,261,402 A | 11/1993 | DiSabito | |
| 5,263,481 A | 11/1993 | Axelgaard et al. | |
| 5,279,607 A | 1/1994 | Schentag et al. | |
| 5,281,287 A | 1/1994 | Lloyd | |
| 5,283,136 A | 2/1994 | Peled et al. | |
| 5,305,745 A | 4/1994 | Zacouto | |
| 5,318,557 A | 6/1994 | Gross | |
| 5,331,953 A | 7/1994 | Andersson et al. | |
| 5,394,882 A | 3/1995 | Mawhinney | |
| 5,395,366 A | 3/1995 | D'Andrea et al. | |
| 5,436,091 A | 7/1995 | Shackle et al. | |
| 5,443,461 A | 8/1995 | Atkinson et al. | |
| 5,443,843 A | 8/1995 | Curatolo et al. | |
| 5,458,141 A | 10/1995 | Neil et al. | |
| 5,458,994 A | 10/1995 | Nesselbeck et al. | |
| 5,485,841 A | 1/1996 | Watkin et al. | |
| 5,506,248 A | 4/1996 | Nikfar et al. | |
| 5,551,020 A | 8/1996 | Flax et al. | |
| 5,567,210 A | 10/1996 | Bates et al. | |
| 5,596,302 A | 1/1997 | Mastrocola et al. | |
| 5,600,548 A | 2/1997 | Nguyen et al. | |
| 5,634,468 A | 6/1997 | Platt | |
| 5,645,063 A | 7/1997 | Straka et al. | |
| 5,659,247 A | 8/1997 | Clements | |
| 5,703,463 A * | 12/1997 | Smith | H01M 10/46 320/134 |
| 5,705,189 A | 1/1998 | Lehmann et al. | |
| 5,724,432 A | 3/1998 | Bouvet et al. | |
| 5,738,708 A | 4/1998 | Peachey et al. | |
| 5,740,811 A | 4/1998 | Hedberg | |
| 5,757,326 A | 5/1998 | Koyama et al. | |
| 5,772,575 A | 6/1998 | Lesinski et al. | |
| 5,792,048 A | 8/1998 | Schaefer | |
| 5,802,467 A | 9/1998 | Salazar | |
| 5,833,716 A | 11/1998 | Bar-Or | |
| 5,842,324 A | 12/1998 | Grosskopf et al. | |
| 5,845,265 A | 12/1998 | Woolston | |
| 5,862,803 A | 1/1999 | Besson | |
| 5,868,136 A | 2/1999 | Fox | |
| 5,925,030 A | 7/1999 | Gross et al. | |
| 5,957,854 A | 9/1999 | Besson et al. | |
| 5,963,132 A | 10/1999 | Yoakum | |
| 5,974,124 A | 10/1999 | Schlueter, Jr. et al. | |
| 5,981,166 A | 11/1999 | Mandecki | |
| 5,999,846 A | 12/1999 | Pardey et al. | |
| 6,018,229 A * | 1/2000 | Mitchell | G06F 1/26 320/112 |
| 6,038,464 A | 3/2000 | Axelgaard et al. | |
| 6,042,710 A | 3/2000 | Dubrow | |
| 6,047,203 A | 4/2000 | Sackner | |
| 6,068,589 A | 5/2000 | Neukermans | |
| 6,076,016 A | 6/2000 | Feierbach et al. | |
| 6,081,734 A | 6/2000 | Batz | |
| 6,091,975 A | 7/2000 | Daddona et al. | |
| 6,095,985 A | 8/2000 | Raymond et al. | |
| 6,115,636 A | 9/2000 | Ryan | |
| 6,122,351 A | 9/2000 | Schlueter, Jr. et al. | |
| 6,141,592 A | 10/2000 | Pauly | |
| 6,149,940 A | 11/2000 | Maggi et al. | |
| 6,200,265 B1 | 3/2001 | Walsh et al. | |
| 6,206,702 B1 | 3/2001 | Hayden et al. | |
| 6,217,744 B1 | 4/2001 | Crosby | |
| 6,231,593 B1 | 5/2001 | Meserol | |
| 6,245,057 B1 | 6/2001 | Sieben et al. | |
| 6,269,058 B1 | 7/2001 | Yamanoi et al. | |
| 6,285,897 B1 | 9/2001 | Kilcoyne et al. | |
| 6,287,252 B1 | 9/2001 | Lugo | |
| 6,288,629 B1 | 9/2001 | Cofino et al. | |
| 6,289,238 B1 | 9/2001 | Besson et al. | |
| 6,315,719 B1 | 11/2001 | Rode et al. | |
| 6,317,714 B1 | 11/2001 | Del Castillo | |
| 6,342,774 B1 | 1/2002 | Kreisinger et al. | |
| 6,344,824 B1 | 2/2002 | Takasugi et al. | |
| 6,358,202 B1 | 3/2002 | Arent | |
| 6,364,834 B1 | 4/2002 | Reuss | |
| 6,366,206 B1 | 4/2002 | Ishikawa et al. | |
| 6,371,927 B1 | 4/2002 | Brune | |
| 6,374,670 B1 | 4/2002 | Spelman | |
| 6,380,858 B1 | 4/2002 | Yarin et al. | |
| 6,390,088 B1 | 5/2002 | Nohl et al. | |
| 6,394,997 B1 | 5/2002 | Lemelson | |
| 6,426,863 B1 | 7/2002 | Munshi | |
| 6,432,292 B1 | 8/2002 | Pinto et al. | |
| 6,440,069 B1 | 8/2002 | Raymond et al. | |
| 6,441,747 B1 | 8/2002 | Khair | |
| 6,453,199 B1 | 9/2002 | Kobozev | |
| 6,477,424 B1 | 11/2002 | Thompson et al. | |
| 6,496,705 B1 | 12/2002 | Ng et al. | |
| 6,526,315 B1 | 2/2003 | Inagawa | |
| 6,531,026 B1 | 3/2003 | Takeichi et al. | |

(56) References Cited

U.S. PATENT DOCUMENTS

| | | |
|---|---|---|
| 6,544,174 B2 | 4/2003 | West |
| 6,564,079 B1 | 5/2003 | Cory |
| 6,567,685 B2 | 5/2003 | Takamori et al. |
| 6,572,636 B1 | 6/2003 | Hagen et al. |
| 6,577,893 B1 | 6/2003 | Besson et al. |
| 6,579,231 B1 | 6/2003 | Phipps |
| 6,595,929 B2 | 7/2003 | Stivoric |
| 6,599,284 B2 | 7/2003 | Faour et al. |
| 6,605,038 B1 | 8/2003 | Teller |
| 6,609,018 B2 | 8/2003 | Cory |
| 6,612,984 B1 | 9/2003 | Kerr |
| 6,632,175 B1 | 10/2003 | Marshall |
| 6,632,216 B2 | 10/2003 | Houzego et al. |
| 6,635,279 B2 | 10/2003 | Kolter et al. |
| 6,643,541 B2 | 11/2003 | Mok et al. |
| 6,654,638 B1 | 11/2003 | Sweeney |
| 6,663,846 B1 | 12/2003 | McCombs |
| 6,673,474 B2 | 1/2004 | Yamamoto |
| 6,680,923 B1 | 1/2004 | Leon |
| 6,689,117 B2 | 2/2004 | Sweeney et al. |
| 6,694,161 B2 | 2/2004 | Mehrotra |
| 6,704,602 B2 | 3/2004 | Berg et al. |
| 6,720,923 B1 | 4/2004 | Hayward et al. |
| 6,738,671 B2 | 5/2004 | Christophersom et al. |
| 6,740,033 B1 | 5/2004 | Olejniczak et al. |
| 6,745,082 B2 | 6/2004 | Axelgaard et al. |
| 6,755,783 B2 | 6/2004 | Cosentino |
| 6,757,523 B2 | 6/2004 | Fry |
| 6,759,968 B2 | 7/2004 | Zierolf |
| 6,773,429 B2 | 8/2004 | Sheppard et al. |
| 6,800,060 B2 | 10/2004 | Marshall |
| 6,801,137 B2 | 10/2004 | Eggers et al. |
| 6,816,794 B2 | 11/2004 | Alvi |
| 6,822,554 B2 | 11/2004 | Vrijens et al. |
| 6,824,512 B2 | 11/2004 | Warkentin et al. |
| 6,836,862 B1 | 12/2004 | Erekson et al. |
| 6,839,659 B2 | 1/2005 | Tarassenko et al. |
| 6,840,904 B2 | 1/2005 | Goldberg |
| 6,842,636 B2 | 1/2005 | Perrault |
| 6,845,272 B1 | 1/2005 | Thomsen |
| 6,864,780 B2 | 3/2005 | Doi |
| 6,879,810 B2 | 4/2005 | Bouet |
| 6,888,337 B2 * | 5/2005 | Sawyers ............... G06F 1/263 320/103 |
| 6,909,878 B2 | 6/2005 | Haller |
| 6,922,592 B2 | 7/2005 | Thompson et al. |
| 6,928,370 B2 | 8/2005 | Anuzis et al. |
| 6,929,636 B1 | 8/2005 | Von Alten |
| 6,937,150 B2 | 8/2005 | Medema |
| 6,942,616 B2 | 9/2005 | Kerr |
| 6,951,536 B2 | 10/2005 | Yokoi |
| 6,957,107 B2 | 10/2005 | Rogers et al. |
| 6,960,617 B2 | 11/2005 | Omidian et al. |
| 6,968,153 B1 | 11/2005 | Heinonen |
| 6,977,511 B2 | 12/2005 | Patel et al. |
| 6,987,965 B2 | 1/2006 | Ng et al. |
| 6,990,082 B1 | 1/2006 | Zehavi et al. |
| 7,002,476 B2 | 2/2006 | Rapchak |
| 7,004,395 B2 | 2/2006 | Koenck |
| 7,009,634 B2 | 3/2006 | Iddan et al. |
| 7,009,946 B1 | 3/2006 | Kardach |
| 7,013,162 B2 | 3/2006 | Gorsuch |
| 7,016,648 B2 | 3/2006 | Haller |
| 7,020,508 B2 | 3/2006 | Stivoric |
| 7,024,248 B2 | 4/2006 | Penner et al. |
| 7,031,745 B2 | 4/2006 | Shen |
| 7,031,857 B2 | 4/2006 | Tarassenko et al. |
| 7,039,453 B2 | 5/2006 | Mullick |
| 7,044,911 B2 | 5/2006 | Drinan et al. |
| 7,046,649 B2 | 5/2006 | Awater et al. |
| 7,083,578 B2 | 8/2006 | Lewkowicz |
| 7,116,252 B2 | 10/2006 | Teraguchi |
| 7,118,531 B2 | 10/2006 | Krill |
| 7,127,300 B2 | 10/2006 | Mazar et al. |
| 7,146,228 B2 | 12/2006 | Nielsen |
| 7,146,449 B2 | 12/2006 | Do et al. |
| 7,149,581 B2 | 12/2006 | Goedeke et al. |
| 7,154,071 B2 | 12/2006 | Sattler et al. |
| 7,155,232 B2 | 12/2006 | Godfrey et al. |
| 7,160,258 B2 | 1/2007 | Imran |
| 7,164,942 B2 | 1/2007 | Avrahami |
| 7,171,166 B2 | 1/2007 | Ng et al. |
| 7,171,177 B2 | 1/2007 | Park et al. |
| 7,171,259 B2 | 1/2007 | Rytky |
| 7,176,784 B2 | 2/2007 | Gilbert et al. |
| 7,187,960 B2 | 3/2007 | Abreu |
| 7,188,199 B2 | 3/2007 | Leung et al. |
| 7,188,767 B2 | 3/2007 | Penuela |
| 7,194,038 B1 | 3/2007 | Inkinen |
| 7,206,630 B1 | 4/2007 | Tarler |
| 7,209,790 B2 | 4/2007 | Thompson et al. |
| 7,215,660 B2 | 5/2007 | Perlman |
| 7,215,991 B2 | 5/2007 | Besson |
| 7,218,967 B2 | 5/2007 | Bergelson |
| 7,231,451 B2 | 6/2007 | Law |
| 7,243,118 B2 | 7/2007 | Lou |
| 7,246,521 B2 | 7/2007 | Kim |
| 7,249,212 B2 | 7/2007 | Do |
| 7,252,792 B2 | 8/2007 | Perrault |
| 7,253,716 B2 | 8/2007 | Lovoi et al. |
| 7,261,690 B2 | 8/2007 | Teller |
| 7,270,633 B1 | 9/2007 | Goscha |
| 7,273,454 B2 | 9/2007 | Raymond et al. |
| 7,289,855 B2 | 10/2007 | Nghiem |
| 7,291,497 B2 | 11/2007 | Holmes |
| 7,292,139 B2 | 11/2007 | Mazar et al. |
| 7,294,105 B1 | 11/2007 | Islam |
| 7,313,163 B2 | 12/2007 | Liu |
| 7,317,378 B2 | 1/2008 | Jarvis et al. |
| 7,318,808 B2 | 1/2008 | Tarassenko et al. |
| 7,336,929 B2 | 2/2008 | Yasuda |
| 7,342,895 B2 | 3/2008 | Serpa |
| 7,346,380 B2 | 3/2008 | Axelgaard et al. |
| 7,349,722 B2 | 3/2008 | Witkowski et al. |
| 7,352,998 B2 | 4/2008 | Palin |
| 7,353,258 B2 | 4/2008 | Washburn |
| 7,357,891 B2 | 4/2008 | Yang et al. |
| 7,359,674 B2 | 4/2008 | Markki |
| 7,366,558 B2 | 4/2008 | Virtanen et al. |
| 7,368,190 B2 | 5/2008 | Heller et al. |
| 7,368,191 B2 | 5/2008 | Andelman et al. |
| 7,373,196 B2 | 5/2008 | Ryu et al. |
| 7,375,739 B2 | 5/2008 | Robbins |
| 7,376,435 B2 | 5/2008 | McGowan |
| 7,382,263 B2 | 6/2008 | Danowski et al. |
| 7,387,607 B2 | 6/2008 | Holt |
| 7,388,903 B2 | 6/2008 | Godfrey et al. |
| 7,389,088 B2 | 6/2008 | Kim |
| 7,392,015 B1 | 6/2008 | Farlow |
| 7,395,106 B2 | 7/2008 | Ryu et al. |
| 7,396,330 B2 | 7/2008 | Banet |
| 7,404,968 B2 | 7/2008 | Abrams et al. |
| 7,413,544 B2 | 8/2008 | Kerr |
| 7,414,534 B1 | 8/2008 | Kroll et al. |
| 7,414,543 B2 | 8/2008 | Rye et al. |
| 7,415,242 B1 | 8/2008 | Ngan |
| 7,424,268 B2 | 9/2008 | Diener |
| 7,424,319 B2 | 9/2008 | Muehlsteff |
| 7,427,266 B2 | 9/2008 | Ayer et al. |
| 7,442,164 B2 | 10/2008 | Berrang et al. |
| 7,471,665 B2 | 12/2008 | Perlman |
| 7,492,128 B2 * | 2/2009 | Shen ............... H02J 7/0063 307/149 |
| 7,499,674 B2 | 3/2009 | Salokannel |
| 7,510,121 B2 | 3/2009 | Koenck |
| 7,512,448 B2 | 3/2009 | Malick |
| 7,515,043 B2 | 4/2009 | Welch |
| 7,519,416 B2 | 4/2009 | Sula et al. |
| 7,523,756 B2 | 4/2009 | Minai |
| 7,525,426 B2 | 4/2009 | Edelstein |
| 7,537,590 B2 | 5/2009 | Santini, Jr. et al. |
| 7,539,533 B2 | 5/2009 | Tran |
| 7,542,878 B2 | 6/2009 | Nanikashvili |
| 7,551,590 B2 | 6/2009 | Haller |

(56) References Cited

U.S. PATENT DOCUMENTS

| | | |
|---|---|---|
| 7,554,452 B2 | 6/2009 | Cole |
| 7,558,620 B2 | 7/2009 | Ishibashi |
| 7,575,005 B2 | 8/2009 | Mumford |
| 7,616,111 B2 | 11/2009 | Covannon |
| 7,617,001 B2 | 11/2009 | Penner et al. |
| 7,626,387 B2 | 12/2009 | Adachi |
| 7,639,473 B2 | 12/2009 | Hsu et al. |
| 7,640,802 B2 | 1/2010 | King et al. |
| 7,645,262 B2 | 1/2010 | Greenberg et al. |
| 7,647,112 B2 | 1/2010 | Tracey |
| 7,647,185 B2 | 1/2010 | Tarassenko et al. |
| 7,653,031 B2 | 1/2010 | Godfrey et al. |
| 7,672,714 B2 | 3/2010 | Kuo |
| 7,673,679 B2 | 3/2010 | Harrison et al. |
| 7,678,043 B2 | 3/2010 | Gilad |
| 7,686,839 B2 | 3/2010 | Parker |
| 7,697,994 B2 | 4/2010 | VanDanacker et al. |
| 7,720,036 B2 | 5/2010 | Sadri |
| 7,729,776 B2 | 6/2010 | Von Arx et al. |
| 7,733,224 B2 | 6/2010 | Tran |
| 7,736,318 B2 | 6/2010 | Cosentino |
| 7,756,587 B2 | 7/2010 | Penner et al. |
| 7,796,043 B2 | 9/2010 | Euliano et al. |
| 7,797,033 B2 | 9/2010 | D'Andrea et al. |
| 7,809,399 B2 | 10/2010 | Lu |
| 7,844,341 B2 | 11/2010 | Von Arx et al. |
| 7,881,799 B2 | 2/2011 | Greenberg et al. |
| 7,978,064 B2 | 7/2011 | Zdeblick et al. |
| 7,983,189 B2 | 7/2011 | Bugenhagen |
| 8,036,731 B2 | 10/2011 | Kimchy et al. |
| 8,036,748 B2 | 10/2011 | Zdeblick et al. |
| 8,054,047 B2 * | 11/2011 | Chen .................... H02J 7/0006 320/107 |
| 8,055,334 B2 | 11/2011 | Savage et al. |
| 8,082,919 B2 | 12/2011 | Brunnberg et al. |
| 8,131,376 B1 | 3/2012 | Faraji et al. |
| 8,200,320 B2 | 6/2012 | Kovacs |
| 8,207,731 B2 | 6/2012 | Moskalenko |
| 8,224,596 B2 | 7/2012 | Agrawal et al. |
| 8,271,146 B2 | 9/2012 | Heber et al. |
| 8,374,698 B2 | 2/2013 | Ok et al. |
| 8,389,003 B2 | 3/2013 | Mintchev et al. |
| 8,404,275 B2 | 3/2013 | Habboushe |
| 8,425,492 B2 | 4/2013 | Herbert et al. |
| 8,443,214 B2 | 5/2013 | Lee et al. |
| 8,532,776 B2 | 9/2013 | Greenberg et al. |
| 8,564,432 B2 | 10/2013 | Covannon et al. |
| 8,597,186 B2 | 12/2013 | Hafezi et al. |
| 8,698,006 B2 | 4/2014 | Bealka et al. |
| 8,758,237 B2 | 6/2014 | Sherman et al. |
| 8,784,308 B2 | 7/2014 | Duck et al. |
| 8,836,513 B2 | 9/2014 | Hafezi et al. |
| 8,858,432 B2 | 10/2014 | Robertson |
| 8,932,221 B2 | 1/2015 | Colliou et al. |
| 8,945,005 B2 | 2/2015 | Hafezi et al. |
| 9,107,806 B2 | 8/2015 | Hafezi et al. |
| 9,119,918 B2 | 9/2015 | Robertson et al. |
| 2001/0027331 A1 | 10/2001 | Thompson |
| 2001/0044588 A1 | 11/2001 | Mault |
| 2001/0051766 A1 | 12/2001 | Gazdzinski |
| 2002/0002326 A1 | 1/2002 | Causey et al. |
| 2002/0026111 A1 | 2/2002 | Ackerman |
| 2002/0032384 A1 | 3/2002 | Raymond et al. |
| 2002/0032385 A1 | 3/2002 | Raymond et al. |
| 2002/0040278 A1 | 4/2002 | Anuzis et al. |
| 2002/0077620 A1 | 6/2002 | Sweeney et al. |
| 2002/0132226 A1 | 9/2002 | Nair |
| 2002/0179921 A1 | 12/2002 | Cohn |
| 2002/0192159 A1 | 12/2002 | Reitberg |
| 2002/0193669 A1 | 12/2002 | Glukhovsky |
| 2002/0198470 A1 | 12/2002 | Imran et al. |
| 2003/0017826 A1 | 1/2003 | Vrijens et al. |
| 2003/0023150 A1 | 1/2003 | Yokoi et al. |
| 2003/0028226 A1 | 2/2003 | Thompson |
| 2003/0062551 A1 | 4/2003 | Chen et al. |
| 2003/0065536 A1 | 4/2003 | Hansen |
| 2003/0076179 A1 | 4/2003 | Branch et al. |
| 2003/0083559 A1 | 5/2003 | Thompson |
| 2003/0126593 A1 | 7/2003 | Mault |
| 2003/0130714 A1 | 7/2003 | Nielsen et al. |
| 2003/0135128 A1 | 7/2003 | Suffin et al. |
| 2003/0135392 A1 | 7/2003 | Vrijens et al. |
| 2003/0152622 A1 | 8/2003 | Louie-Helm et al. |
| 2003/0158466 A1 | 8/2003 | Lynn et al. |
| 2003/0158756 A1 | 8/2003 | Abramson |
| 2003/0162556 A1 | 8/2003 | Libes |
| 2003/0164401 A1 | 9/2003 | Andreasson et al. |
| 2003/0167000 A1 | 9/2003 | Mullick et al. |
| 2003/0171791 A1 | 9/2003 | KenKnight |
| 2003/0171898 A1 | 9/2003 | Tarassenko et al. |
| 2003/0181788 A1 | 9/2003 | Yokoi et al. |
| 2003/0185286 A1 | 10/2003 | Yuen |
| 2003/0187337 A1 | 10/2003 | Tarassenko et al. |
| 2003/0187338 A1 | 10/2003 | Say et al. |
| 2003/0195403 A1 | 10/2003 | Berner et al. |
| 2003/0213495 A1 | 11/2003 | Fujita et al. |
| 2003/0214579 A1 | 11/2003 | Iddan |
| 2003/0216622 A1 | 11/2003 | Meron et al. |
| 2003/0216625 A1 | 11/2003 | Phipps |
| 2003/0216666 A1 | 11/2003 | Ericson et al. |
| 2003/0216729 A1 | 11/2003 | Marchitto |
| 2003/0232895 A1 | 12/2003 | Omidian et al. |
| 2004/0008123 A1 | 1/2004 | Carrender et al. |
| 2004/0018476 A1 | 1/2004 | LaDue |
| 2004/0034295 A1 | 2/2004 | Salganicoff |
| 2004/0049245 A1 | 3/2004 | Gass |
| 2004/0073095 A1 | 4/2004 | Causey et al. |
| 2004/0073454 A1 | 4/2004 | Urquhart et al. |
| 2004/0077995 A1 | 4/2004 | Ferek-Petric |
| 2004/0082982 A1 | 4/2004 | Gord et al. |
| 2004/0087839 A1 | 5/2004 | Raymond et al. |
| 2004/0092801 A1 | 5/2004 | Drakulic |
| 2004/0106859 A1 | 6/2004 | Say et al. |
| 2004/0115507 A1 | 6/2004 | Potter et al. |
| 2004/0115517 A1 | 6/2004 | Fukada et al. |
| 2004/0121015 A1 | 6/2004 | Chidlaw et al. |
| 2004/0148140 A1 | 7/2004 | Tarassenko et al. |
| 2004/0153007 A1 | 8/2004 | Harris |
| 2004/0167226 A1 | 8/2004 | Serafini |
| 2004/0167801 A1 | 8/2004 | Say et al. |
| 2004/0193020 A1 | 9/2004 | Chiba |
| 2004/0193029 A1 | 9/2004 | Gluhovsky |
| 2004/0193446 A1 | 9/2004 | Mayer et al. |
| 2004/0199222 A1 | 10/2004 | Sun et al. |
| 2004/0215084 A1 | 10/2004 | Shimizu et al. |
| 2004/0218683 A1 | 11/2004 | Batra |
| 2004/0220643 A1 | 11/2004 | Schmidt |
| 2004/0224644 A1 | 11/2004 | Wu |
| 2004/0225199 A1 | 11/2004 | Evanyk |
| 2004/0253304 A1 | 12/2004 | Gross et al. |
| 2004/0258571 A1 | 12/2004 | Lee et al. |
| 2004/0260154 A1 | 12/2004 | Sidelnik |
| 2005/0003074 A1 | 1/2005 | Brown et al. |
| 2005/0017841 A1 | 1/2005 | Doi |
| 2005/0020887 A1 | 1/2005 | Goldberg |
| 2005/0021370 A1 | 1/2005 | Riff |
| 2005/0024198 A1 | 2/2005 | Ward |
| 2005/0027205 A1 | 2/2005 | Tarassenko et al. |
| 2005/0038321 A1 | 2/2005 | Fujita et al. |
| 2005/0043634 A1 | 2/2005 | Yokoi et al. |
| 2005/0043894 A1 | 2/2005 | Fernandez |
| 2005/0054897 A1 | 3/2005 | Hashimoto et al. |
| 2005/0055014 A1 | 3/2005 | Coppeta et al. |
| 2005/0062644 A1 | 3/2005 | Leci |
| 2005/0065407 A1 | 3/2005 | Nakamura |
| 2005/0070778 A1 | 3/2005 | Lackey et al. |
| 2005/0075145 A1 | 4/2005 | Dvorak et al. |
| 2005/0090753 A1 | 4/2005 | Goor et al. |
| 2005/0092108 A1 | 5/2005 | Andermo |
| 2005/0096514 A1 | 5/2005 | Starkebaum |
| 2005/0096562 A1 | 5/2005 | Delalic et al. |
| 2005/0101843 A1 | 5/2005 | Quinn |
| 2005/0101872 A1 | 5/2005 | Sattler |
| 2005/0115561 A1 | 6/2005 | Stahmann et al. |

(56) References Cited

U.S. PATENT DOCUMENTS

| | | |
|---|---|---|
| 2005/0116820 A1 | 6/2005 | Goldreich |
| 2005/0117389 A1 | 6/2005 | Worledge |
| 2005/0121322 A1 | 6/2005 | Say et al. |
| 2005/0131281 A1 | 6/2005 | Ayer et al. |
| 2005/0143623 A1 | 6/2005 | Kojima |
| 2005/0146594 A1 | 7/2005 | Nakatani et al. |
| 2005/0148883 A1 | 7/2005 | Boesen |
| 2005/0154428 A1 | 7/2005 | Bruinsma |
| 2005/0156709 A1 | 7/2005 | Gilbert et al. |
| 2005/0165323 A1 | 7/2005 | Montgomery |
| 2005/0177069 A1 | 8/2005 | Takizawa |
| 2005/0182389 A1 | 8/2005 | LaPorte |
| 2005/0187789 A1 | 8/2005 | Hatlestad et al. |
| 2005/0192489 A1 | 9/2005 | Marshall |
| 2005/0197680 A1 | 9/2005 | DelMain et al. |
| 2005/0208251 A1 | 9/2005 | Aisenbrey |
| 2005/0228268 A1 | 10/2005 | Cole |
| 2005/0234307 A1 | 10/2005 | Heinonen |
| 2005/0240305 A1 | 10/2005 | Bogash et al. |
| 2005/0245794 A1 | 11/2005 | Dinsmoor |
| 2005/0259768 A1 | 11/2005 | Yang et al. |
| 2005/0261559 A1 | 11/2005 | Mumford |
| 2005/0267556 A1 | 12/2005 | Shuros et al. |
| 2005/0267756 A1 | 12/2005 | Schultz et al. |
| 2005/0277912 A1 | 12/2005 | John |
| 2005/0277999 A1 | 12/2005 | Strother et al. |
| 2005/0279054 A1 | 12/2005 | Mauze et al. |
| 2005/0280539 A1 | 12/2005 | Pettus |
| 2005/0285746 A1 | 12/2005 | Sengupta |
| 2005/0288594 A1 | 12/2005 | Lewkowicz et al. |
| 2006/0001496 A1 | 1/2006 | Abrosimov et al. |
| 2006/0028727 A1 | 2/2006 | Moon et al. |
| 2006/0036134 A1 | 2/2006 | Tarassenko et al. |
| 2006/0058602 A1 | 3/2006 | Kwiatkowski et al. |
| 2006/0061472 A1 | 3/2006 | Lovoi et al. |
| 2006/0065713 A1 | 3/2006 | Kingery |
| 2006/0068006 A1 | 3/2006 | Begleiter |
| 2006/0074283 A1 | 4/2006 | Henderson |
| 2006/0074319 A1 | 4/2006 | Barnes et al. |
| 2006/0078765 A1 | 4/2006 | Yang et al. |
| 2006/0095091 A1 | 5/2006 | Drew |
| 2006/0095093 A1 | 5/2006 | Bettesh et al. |
| 2006/0100533 A1 | 5/2006 | Han |
| 2006/0109058 A1 | 5/2006 | Keating |
| 2006/0110962 A1 | 5/2006 | Powell |
| 2006/0122474 A1 | 6/2006 | Teller et al. |
| 2006/0122667 A1 | 6/2006 | Chavan et al. |
| 2006/0136266 A1 | 6/2006 | Tarassenko et al. |
| 2006/0142648 A1 | 6/2006 | Banet |
| 2006/0145876 A1 | 7/2006 | Kimura |
| 2006/0148254 A1 | 7/2006 | McLean |
| 2006/0149339 A1 | 7/2006 | Burnes |
| 2006/0155174 A1 | 7/2006 | Glukhovsky et al. |
| 2006/0155183 A1 | 7/2006 | Kroecker |
| 2006/0161225 A1 | 7/2006 | Sormann et al. |
| 2006/0179949 A1 | 8/2006 | Kim |
| 2006/0183993 A1 | 8/2006 | Horn |
| 2006/0184092 A1 | 8/2006 | Atanasoska et al. |
| 2006/0204738 A1 | 9/2006 | Dubrow et al. |
| 2006/0210626 A1 | 9/2006 | Spaeder |
| 2006/0216603 A1 | 9/2006 | Choi |
| 2006/0218011 A1 | 9/2006 | Walker |
| 2006/0235489 A1 | 10/2006 | Drew |
| 2006/0243288 A1 | 11/2006 | Kim et al. |
| 2006/0247505 A1 | 11/2006 | Siddiqui |
| 2006/0253005 A1 | 11/2006 | Drinan |
| 2006/0270346 A1 | 11/2006 | Ibrahim |
| 2006/0273882 A1 | 12/2006 | Posamentier |
| 2006/0276702 A1 | 12/2006 | McGinnis |
| 2006/0280227 A1 | 12/2006 | Pinkney |
| 2006/0282001 A1 | 12/2006 | Noel |
| 2006/0289640 A1 | 12/2006 | Mercure |
| 2006/0293607 A1 | 12/2006 | Alt |
| 2007/0000776 A1 | 1/2007 | Karube et al. |
| 2007/0002038 A1 | 1/2007 | Suzuki |
| 2007/0006636 A1 | 1/2007 | King et al. |
| 2007/0008113 A1 | 1/2007 | Spoonhower et al. |
| 2007/0016089 A1 | 1/2007 | Fischell et al. |
| 2007/0027386 A1 | 2/2007 | Such |
| 2007/0027388 A1 | 2/2007 | Chou |
| 2007/0038054 A1 | 2/2007 | Zhou |
| 2007/0049339 A1 | 3/2007 | Barak et al. |
| 2007/0055098 A1 | 3/2007 | Shimizu et al. |
| 2007/0060797 A1 | 3/2007 | Ball |
| 2007/0060800 A1 | 3/2007 | Drinan et al. |
| 2007/0066929 A1 | 3/2007 | Ferren et al. |
| 2007/0073353 A1 | 3/2007 | Rooney et al. |
| 2007/0096765 A1 | 5/2007 | Kagan |
| 2007/0106346 A1 | 5/2007 | Bergelson |
| 2007/0123772 A1 | 5/2007 | Euliano |
| 2007/0129622 A1 | 6/2007 | Bourget |
| 2007/0130287 A1 | 6/2007 | Kumar |
| 2007/0135803 A1 | 6/2007 | Belson |
| 2007/0142721 A1 | 6/2007 | Berner et al. |
| 2007/0156016 A1 | 7/2007 | Betesh |
| 2007/0160789 A1 | 7/2007 | Merical |
| 2007/0162089 A1 | 7/2007 | Mosesov |
| 2007/0162090 A1 | 7/2007 | Penner |
| 2007/0167495 A1 | 7/2007 | Brown et al. |
| 2007/0167848 A1 | 7/2007 | Kuo et al. |
| 2007/0173701 A1 | 7/2007 | Al-Ali |
| 2007/0179347 A1 | 8/2007 | Tarassenko et al. |
| 2007/0179371 A1 | 8/2007 | Peyser et al. |
| 2007/0185393 A1 | 8/2007 | Zhou |
| 2007/0191002 A1 | 8/2007 | Ge |
| 2007/0196456 A1 | 8/2007 | Stevens |
| 2007/0207793 A1 | 9/2007 | Myer |
| 2007/0208233 A1 | 9/2007 | Kovacs |
| 2007/0213659 A1 | 9/2007 | Trovato et al. |
| 2007/0237719 A1 | 10/2007 | Jones |
| 2007/0244370 A1 | 10/2007 | Kuo et al. |
| 2007/0255198 A1 | 11/2007 | Leong et al. |
| 2007/0255330 A1 | 11/2007 | Lee |
| 2007/0270672 A1 | 11/2007 | Hayter |
| 2007/0279217 A1 | 12/2007 | Venkatraman |
| 2007/0282174 A1 | 12/2007 | Sabatino |
| 2007/0282177 A1 | 12/2007 | Pilz |
| 2007/0299480 A1 | 12/2007 | Hill |
| 2008/0014866 A1 | 1/2008 | Lipowshi |
| 2008/0020037 A1 | 1/2008 | Robertson et al. |
| 2008/0021519 A1 | 1/2008 | DeGeest |
| 2008/0021521 A1 | 1/2008 | Shah |
| 2008/0027679 A1 | 1/2008 | Shklarski |
| 2008/0033273 A1 | 2/2008 | Zhou |
| 2008/0038588 A1 | 2/2008 | Lee |
| 2008/0039700 A1 | 2/2008 | Drinan |
| 2008/0045843 A1 | 2/2008 | Tsuji et al. |
| 2008/0046038 A1 | 2/2008 | Hill |
| 2008/0051647 A1 | 2/2008 | Wu et al. |
| 2008/0051667 A1 | 2/2008 | Goldreich |
| 2008/0058614 A1 | 3/2008 | Banet |
| 2008/0062856 A1 | 3/2008 | Feher |
| 2008/0065168 A1 | 3/2008 | Bitton et al. |
| 2008/0074307 A1 | 3/2008 | Boric-Lubecke |
| 2008/0077015 A1 | 3/2008 | Boric-Lubecke |
| 2008/0077028 A1 | 3/2008 | Schaldach et al. |
| 2008/0077188 A1 | 3/2008 | Denker et al. |
| 2008/0091089 A1 | 4/2008 | Guillory et al. |
| 2008/0091114 A1 | 4/2008 | Min |
| 2008/0097549 A1 | 4/2008 | Colbaugh |
| 2008/0097917 A1 | 4/2008 | Dicks |
| 2008/0103440 A1 | 5/2008 | Ferren et al. |
| 2008/0112885 A1 | 5/2008 | Okunev et al. |
| 2008/0114224 A1 | 5/2008 | Bandy et al. |
| 2008/0119705 A1 | 5/2008 | Patel |
| 2008/0119716 A1 | 5/2008 | Boric-Lubecke |
| 2008/0121825 A1 | 5/2008 | Trovato et al. |
| 2008/0137566 A1 | 6/2008 | Marholev |
| 2008/0139907 A1 | 6/2008 | Rao et al. |
| 2008/0140403 A1 | 6/2008 | Hughes et al. |
| 2008/0146871 A1 | 6/2008 | Arneson et al. |
| 2008/0146889 A1 | 6/2008 | Young |
| 2008/0146892 A1 | 6/2008 | LeBeouf |
| 2008/0154104 A1 | 6/2008 | Lamego |

(56) References Cited

U.S. PATENT DOCUMENTS

| | | |
|---|---|---|
| 2008/0166992 A1 | 7/2008 | Ricordi |
| 2008/0175898 A1 | 7/2008 | Jones et al. |
| 2008/0183245 A1 | 7/2008 | Van Oort |
| 2008/0188837 A1 | 8/2008 | Belsky et al. |
| 2008/0194912 A1 | 8/2008 | Trovato et al. |
| 2008/0208009 A1 | 8/2008 | Shklarski |
| 2008/0214901 A1 | 9/2008 | Gehman |
| 2008/0214985 A1 | 9/2008 | Yanaki |
| 2008/0243020 A1 | 10/2008 | Chou |
| 2008/0249360 A1 | 10/2008 | Li |
| 2008/0262320 A1 | 10/2008 | Schaefer et al. |
| 2008/0262336 A1 | 10/2008 | Ryu |
| 2008/0269664 A1 | 10/2008 | Trovato et al. |
| 2008/0275312 A1 | 11/2008 | Mosesov |
| 2008/0284599 A1 | 11/2008 | Zdeblick et al. |
| 2008/0288027 A1 | 11/2008 | Kroll |
| 2008/0294020 A1 | 11/2008 | Sapounas |
| 2008/0299197 A1 | 12/2008 | Toneguzzo et al. |
| 2008/0300572 A1 | 12/2008 | Rankers |
| 2008/0303638 A1 | 12/2008 | Nguyen |
| 2008/0306357 A1 | 12/2008 | Korman |
| 2008/0306359 A1 | 12/2008 | Zdeblick et al. |
| 2008/0306360 A1 | 12/2008 | Robertson et al. |
| 2008/0311852 A1 | 12/2008 | Hansen |
| 2008/0312522 A1 | 12/2008 | Rowlandson |
| 2008/0316020 A1 | 12/2008 | Robertson |
| 2009/0009330 A1 | 1/2009 | Sakama et al. |
| 2009/0009332 A1 | 1/2009 | Nunez et al. |
| 2009/0024045 A1 | 1/2009 | Prakash |
| 2009/0024112 A1 | 1/2009 | Edwards et al. |
| 2009/0030293 A1 | 1/2009 | Cooper et al. |
| 2009/0030297 A1 | 1/2009 | Miller |
| 2009/0034209 A1 | 2/2009 | Joo |
| 2009/0043171 A1 | 2/2009 | Rule |
| 2009/0048498 A1 | 2/2009 | Riskey |
| 2009/0062634 A1 | 3/2009 | Say et al. |
| 2009/0062670 A1 | 3/2009 | Sterling |
| 2009/0069642 A1 | 3/2009 | Gao |
| 2009/0069655 A1 | 3/2009 | Say et al. |
| 2009/0069656 A1 | 3/2009 | Say et al. |
| 2009/0069657 A1 | 3/2009 | Say et al. |
| 2009/0069658 A1 | 3/2009 | Say et al. |
| 2009/0069724 A1 | 3/2009 | Otto et al. |
| 2009/0076343 A1 | 3/2009 | James |
| 2009/0082645 A1 | 3/2009 | Hafezi et al. |
| 2009/0087483 A1 | 4/2009 | Sison |
| 2009/0088618 A1 | 4/2009 | Ameson |
| 2009/0099435 A1 | 4/2009 | Say et al. |
| 2009/0105561 A1 | 4/2009 | Boydon et al. |
| 2009/0110148 A1 | 4/2009 | Zhang |
| 2009/0112626 A1 | 4/2009 | Talbot |
| 2009/0124871 A1 | 5/2009 | Arshak |
| 2009/0124965 A1 | 5/2009 | Greenberg et al. |
| 2009/0131774 A1 | 5/2009 | Sweitzer |
| 2009/0135886 A1 | 5/2009 | Robertson et al. |
| 2009/0142853 A1 | 6/2009 | Warrington et al. |
| 2009/0149839 A1 | 6/2009 | Hyde et al. |
| 2009/0157113 A1 | 6/2009 | Marcotte |
| 2009/0157358 A1 | 6/2009 | Kim |
| 2009/0161602 A1 | 6/2009 | Matsumoto |
| 2009/0163789 A1 | 6/2009 | Say et al. |
| 2009/0171180 A1 | 7/2009 | Pering |
| 2009/0171420 A1 | 7/2009 | Brown et al. |
| 2009/0173628 A1 | 7/2009 | Say et al. |
| 2009/0177055 A1 | 7/2009 | Say et al. |
| 2009/0177056 A1 | 7/2009 | Say et al. |
| 2009/0177057 A1 | 7/2009 | Say et al. |
| 2009/0177058 A1 | 7/2009 | Say et al. |
| 2009/0177059 A1 | 7/2009 | Say et al. |
| 2009/0177060 A1 | 7/2009 | Say et al. |
| 2009/0177061 A1 | 7/2009 | Say et al. |
| 2009/0177062 A1 | 7/2009 | Say et al. |
| 2009/0177063 A1 | 7/2009 | Say et al. |
| 2009/0177064 A1 | 7/2009 | Say et al. |
| 2009/0177065 A1 | 7/2009 | Say et al. |
| 2009/0177066 A1 | 7/2009 | Say et al. |
| 2009/0182206 A1 | 7/2009 | Najafi |
| 2009/0182207 A1 | 7/2009 | Riskey et al. |
| 2009/0182212 A1 | 7/2009 | Say et al. |
| 2009/0182213 A1 | 7/2009 | Say et al. |
| 2009/0182214 A1 | 7/2009 | Say et al. |
| 2009/0182215 A1 | 7/2009 | Say et al. |
| 2009/0182388 A1 | 7/2009 | Von Arx |
| 2009/0187088 A1 | 7/2009 | Say et al. |
| 2009/0187089 A1 | 7/2009 | Say et al. |
| 2009/0187090 A1 | 7/2009 | Say et al. |
| 2009/0187091 A1 | 7/2009 | Say et al. |
| 2009/0187092 A1 | 7/2009 | Say et al. |
| 2009/0187093 A1 | 7/2009 | Say et al. |
| 2009/0187094 A1 | 7/2009 | Say et al. |
| 2009/0187095 A1 | 7/2009 | Say et al. |
| 2009/0187381 A1 | 7/2009 | King et al. |
| 2009/0192351 A1 | 7/2009 | Nishino |
| 2009/0192368 A1 | 7/2009 | Say et al. |
| 2009/0192369 A1 | 7/2009 | Say et al. |
| 2009/0192370 A1 | 7/2009 | Say et al. |
| 2009/0192371 A1 | 7/2009 | Say et al. |
| 2009/0192372 A1 | 7/2009 | Say et al. |
| 2009/0192373 A1 | 7/2009 | Say et al. |
| 2009/0192374 A1 | 7/2009 | Say et al. |
| 2009/0192375 A1 | 7/2009 | Say et al. |
| 2009/0192376 A1 | 7/2009 | Say et al. |
| 2009/0192377 A1 | 7/2009 | Say et al. |
| 2009/0192378 A1 | 7/2009 | Say et al. |
| 2009/0192379 A1 | 7/2009 | Say et al. |
| 2009/0198115 A1 | 8/2009 | Say et al. |
| 2009/0198116 A1 | 8/2009 | Say et al. |
| 2009/0198175 A1 | 8/2009 | Say et al. |
| 2009/0203964 A1 | 8/2009 | Shimizu et al. |
| 2009/0203971 A1 | 8/2009 | Sciarappa |
| 2009/0203972 A1 | 8/2009 | Heneghan |
| 2009/0203978 A1 | 8/2009 | Say et al. |
| 2009/0204265 A1 | 8/2009 | Hackett |
| 2009/0210164 A1 | 8/2009 | Say et al. |
| 2009/0216101 A1 | 8/2009 | Say et al. |
| 2009/0216102 A1 | 8/2009 | Say et al. |
| 2009/0227204 A1 | 9/2009 | Robertson et al. |
| 2009/0227876 A1 | 9/2009 | Tran |
| 2009/0227940 A1 | 9/2009 | Say et al. |
| 2009/0227941 A1 | 9/2009 | Say et al. |
| 2009/0227988 A1 | 9/2009 | Wood et al. |
| 2009/0228214 A1 | 9/2009 | Say et al. |
| 2009/0231125 A1 | 9/2009 | Baldus |
| 2009/0234200 A1 | 9/2009 | Husheer |
| 2009/0243833 A1 | 10/2009 | Huang |
| 2009/0253960 A1 | 10/2009 | Takenaka et al. |
| 2009/0256702 A1 | 10/2009 | Robertson |
| 2009/0260212 A1 | 10/2009 | Schmett et al. |
| 2009/0264714 A1 | 10/2009 | Chou |
| 2009/0264964 A1 | 10/2009 | Abrahamson |
| 2009/0265186 A1 | 10/2009 | Tarassenko et al. |
| 2009/0273467 A1 | 11/2009 | Elixmann |
| 2009/0281539 A1 | 11/2009 | Selig |
| 2009/0295548 A1 | 12/2009 | Ronkka |
| 2009/0296677 A1 | 12/2009 | Mahany |
| 2009/0303920 A1 | 12/2009 | Mahany |
| 2009/0306633 A1 | 12/2009 | Trovato et al. |
| 2009/0312619 A1 | 12/2009 | Say et al. |
| 2009/0318303 A1 | 12/2009 | Delamarche et al. |
| 2009/0318761 A1 | 12/2009 | Rabinovitz |
| 2009/0318779 A1 | 12/2009 | Tran |
| 2009/0318783 A1 | 12/2009 | Rohde |
| 2009/0318793 A1 | 12/2009 | Datta |
| 2010/0001841 A1 | 1/2010 | Cardullo |
| 2010/0010330 A1 | 1/2010 | Rankers |
| 2010/0033324 A1 | 2/2010 | Shimizu et al. |
| 2010/0049004 A1 | 2/2010 | Edman et al. |
| 2010/0049006 A1 | 2/2010 | Magar |
| 2010/0049012 A1 | 2/2010 | Dijksman et al. |
| 2010/0049069 A1 | 2/2010 | Tarassenko et al. |
| 2010/0056878 A1 | 3/2010 | Partin |
| 2010/0056891 A1 | 3/2010 | Say et al. |
| 2010/0056939 A1 | 3/2010 | Tarassenko et al. |
| 2010/0057041 A1 | 3/2010 | Hayter |

(56) References Cited

U.S. PATENT DOCUMENTS

| | | |
|---|---|---|
| 2010/0062709 A1 | 3/2010 | Kato |
| 2010/0063438 A1 | 3/2010 | Bengtsson |
| 2010/0063841 A1 | 3/2010 | D'Ambrosia et al. |
| 2010/0069002 A1 | 3/2010 | Rong |
| 2010/0069717 A1 | 3/2010 | Hafezi et al. |
| 2010/0099967 A1 | 4/2010 | Say et al. |
| 2010/0099968 A1 | 4/2010 | Say et al. |
| 2010/0099969 A1 | 4/2010 | Say et al. |
| 2010/0100077 A1 | 4/2010 | Rush |
| 2010/0100078 A1 | 4/2010 | Say et al. |
| 2010/0106001 A1 | 4/2010 | Say et al. |
| 2010/0118853 A1 | 5/2010 | Godfrey |
| 2010/0139672 A1 | 6/2010 | Kroll et al. |
| 2010/0168659 A1 | 7/2010 | Say et al. |
| 2010/0179398 A1 | 7/2010 | Say et al. |
| 2010/0191073 A1 | 7/2010 | Tarassenko et al. |
| 2010/0210299 A1 | 8/2010 | Gorbachov |
| 2010/0222652 A1 | 9/2010 | Cho |
| 2010/0228113 A1 | 9/2010 | Solosko |
| 2010/0233026 A1 | 9/2010 | Ismagliov et al. |
| 2010/0234706 A1 | 9/2010 | Gilland |
| 2010/0234715 A1 | 9/2010 | Shin |
| 2010/0234914 A1 | 9/2010 | Shen |
| 2010/0245091 A1 | 9/2010 | Singh |
| 2010/0249881 A1 | 9/2010 | Corndorf |
| 2010/0256461 A1 | 10/2010 | Mohamedali |
| 2010/0259543 A1 | 10/2010 | Tarassenko et al. |
| 2010/0268048 A1 | 10/2010 | Say et al. |
| 2010/0268049 A1 | 10/2010 | Say et al. |
| 2010/0268050 A1 | 10/2010 | Say et al. |
| 2010/0274111 A1 | 10/2010 | Say et al. |
| 2010/0280345 A1 | 11/2010 | Say et al. |
| 2010/0280346 A1 | 11/2010 | Say et al. |
| 2010/0295694 A1 | 11/2010 | Kauffman et al. |
| 2010/0297640 A1 | 11/2010 | Kumar et al. |
| 2010/0298650 A1 | 11/2010 | Moon et al. |
| 2010/0298668 A1 | 11/2010 | Hafezi et al. |
| 2010/0298730 A1 | 11/2010 | Tarassenko et al. |
| 2010/0312188 A1 | 12/2010 | Robertson et al. |
| 2010/0312580 A1 | 12/2010 | Tarassenko et al. |
| 2011/0009715 A1 | 1/2011 | O'Reilly et al. |
| 2011/0054265 A1 | 3/2011 | Hafezi et al. |
| 2011/0065983 A1 | 3/2011 | Hafezi et al. |
| 2011/0077660 A1 | 3/2011 | Janik et al. |
| 2011/0105864 A1 | 5/2011 | Robertson et al. |
| 2011/0124983 A1 | 5/2011 | Kroll et al. |
| 2011/0224912 A1 | 9/2011 | Bhavaraju et al. |
| 2011/0230732 A1 | 9/2011 | Edman et al. |
| 2012/0016231 A1 | 1/2012 | Westmoreland |
| 2012/0059257 A1 | 3/2012 | Duck et al. |
| 2012/0062371 A1 | 3/2012 | Radivojevic et al. |
| 2012/0245043 A1 | 9/2012 | England |
| 2012/0299723 A1 | 11/2012 | Hafezi et al. |
| 2013/0030366 A1 | 1/2013 | Robertson et al. |
| 2013/0129869 A1 | 5/2013 | Hafezi et al. |
| 2013/0144132 A1 | 6/2013 | Hafezi et al. |
| 2015/0059922 A1 | 3/2015 | Thompson et al. |
| 2015/0080677 A1 | 3/2015 | Thompson et al. |
| 2015/0080678 A1 | 3/2015 | Frank et al. |
| 2015/0080679 A1 | 3/2015 | Frank et al. |
| 2015/0080680 A1 | 3/2015 | Zdeblick et al. |
| 2015/0080681 A1 | 3/2015 | Hafezi et al. |
| 2015/0112243 A1 | 4/2015 | Hafezi et al. |
| 2015/0127737 A1 | 5/2015 | Thompson et al. |
| 2015/0127738 A1 | 5/2015 | Thompson et al. |
| 2015/0150480 A1 | 6/2015 | Zdeblick et al. |
| 2015/0164746 A1 | 6/2015 | Costello et al. |
| 2015/0173646 A1 | 6/2015 | Berkman et al. |
| 2015/0223751 A1 | 8/2015 | Zdeblick et al. |
| 2015/0230729 A1 | 8/2015 | Zdeblick et al. |
| 2015/0248833 A1 | 9/2015 | Arne et al. |

FOREIGN PATENT DOCUMENTS

| | | |
|---|---|---|
| EP | 0344939 | 12/1989 |
| EP | 1246356 | 10/2002 |
| EP | 1534054 | 5/2005 |
| EP | 1702553 | 9/2006 |
| EP | 1244308 | 12/2007 |
| EP | 2143369 | 1/2010 |
| JP | 61072712 | 4/1986 |
| JP | 05-228128 | 9/1993 |
| JP | 2000-506410 | 5/2000 |
| JP | 2002263185 | 9/2002 |
| JP | 2002282219 | 10/2002 |
| JP | 2003050867 | 2/2003 |
| JP | 2004-313242 | 11/2004 |
| JP | 2005-073886 | 3/2005 |
| JP | 2005-087552 | 4/2005 |
| JP | 2005-304880 | 4/2005 |
| JP | 2005124708 | 5/2005 |
| JP | 2005514966 | 5/2005 |
| JP | 2005343513 | 12/2005 |
| JP | 2006006377 | 1/2006 |
| JP | 2006509574 | 3/2006 |
| JP | 2007-313340 | 12/2007 |
| JP | 2009514870 | 4/2009 |
| JP | 2009528909 | 8/2009 |
| KR | 2006077523 | 7/2006 |
| TV | 200916136 | 4/2009 |
| TW | 200406192 | 5/2004 |
| WO | WO 8802237 | 4/1988 |
| WO | WO9221307 | 12/1992 |
| WO | WO9308734 | 5/1993 |
| WO | WO9319667 | 10/1993 |
| WO | WO9401165 | 1/1994 |
| WO | WO9709963 | 10/1997 |
| WO | WO9843537 | 10/1998 |
| WO | WO9937290 | 7/1999 |
| WO | WO9959465 | 11/1999 |
| WO | WO0033246 | 6/2000 |
| WO | WO0147466 | 7/2001 |
| WO | WO0174011 | 10/2001 |
| WO | WO0180731 | 11/2001 |
| WO | WO0245489 | 6/2002 |
| WO | WO02058330 | 7/2002 |
| WO | WO02062276 | 8/2002 |
| WO | WO02087681 | 11/2002 |
| WO | WO02095351 | 11/2002 |
| WO | WO03005877 | 1/2003 |
| WO | WO03050643 | 6/2003 |
| WO | WO03068061 | 8/2003 |
| WO | WO2004014225 | 2/2004 |
| WO | WO2004019172 | 3/2004 |
| WO | WO2004039256 | 5/2004 |
| WO | WO2004066833 | 8/2004 |
| WO | WO2004066834 | 8/2004 |
| WO | WO2004066903 | 8/2004 |
| WO | WO2004068881 | 8/2004 |
| WO | WO2004075032 | 9/2004 |
| WO | WO2004109316 | 12/2004 |
| WO | WO2005011237 | 2/2005 |
| WO | WO2005020023 | 3/2005 |
| WO | WO2005024687 | 3/2005 |
| WO | WO2005041438 | 5/2005 |
| WO | WO2005047837 | 5/2005 |
| WO | WO2005051166 | 6/2005 |
| WO | WO2005053517 | 6/2005 |
| WO | WO2005083621 | 9/2005 |
| WO | WO2005110238 | 11/2005 |
| WO | WO2006021932 | 3/2006 |
| WO | WO2006027586 | 3/2006 |
| WO | WO2006028347 | 3/2006 |
| WO | WO2006055892 | 5/2006 |
| WO | WO2006055956 | 5/2006 |
| WO | WO2006075016 | 7/2006 |
| WO | WO2006100620 | 9/2006 |
| WO | WO2006116718 | 11/2006 |
| WO | WO2006127355 | 11/2006 |
| WO | WO2007001724 | 1/2007 |
| WO | WO2007001742 | 1/2007 |

(56) References Cited

FOREIGN PATENT DOCUMENTS

| | | |
|---|---|---|
| WO | WO2007013952 | 2/2007 |
| WO | WO2007014084 | 2/2007 |
| WO | WO2007014527 | 2/2007 |
| WO | WO2007021496 | 2/2007 |
| WO | WO2007027660 | 3/2007 |
| WO | WO2007028035 | 3/2007 |
| WO | WO2007036687 | 4/2007 |
| WO | WO2007036741 | 4/2007 |
| WO | WO2007036746 | 4/2007 |
| WO | WO2007040878 | 4/2007 |
| WO | WO2007067054 | 6/2007 |
| WO | WO2007071180 | 6/2007 |
| WO | WO2007096810 | 8/2007 |
| WO | WO2007101141 | 9/2007 |
| WO | WO2007115087 | 10/2007 |
| WO | WO2007120946 | 10/2007 |
| WO | WO2007127316 | 11/2007 |
| WO | WO2007127879 | 11/2007 |
| WO | WO2007128165 | 11/2007 |
| WO | WO2007130491 | 11/2007 |
| WO | WO2007143535 | 12/2007 |
| WO | WO2007149546 | 12/2007 |
| WO | WO2006104843 | 1/2008 |
| WO | WO2008008281 | 1/2008 |
| WO | WO2008012700 | 1/2008 |
| WO | WO2008030482 | 3/2008 |
| WO | WO2008052136 | 5/2008 |
| WO | WO2008063626 | 5/2008 |
| WO | WO2008066617 | 6/2008 |
| WO | WO2008076464 | 6/2008 |
| WO | WO2008089232 | 7/2008 |
| WO | WO2008091683 | 7/2008 |
| WO | WO2008095183 | 8/2008 |
| WO | WO2008097652 | 8/2008 |
| WO | WO2008101107 | 8/2008 |
| WO | WO2008112577 | 9/2008 |
| WO | WO2008112578 | 9/2008 |
| WO | WO2008120156 | 10/2008 |
| WO | WO2008133394 | 11/2008 |
| WO | WO2008134185 | 11/2008 |
| WO | WO2008150633 | 12/2008 |
| WO | WO2009000447 | 12/2008 |
| WO | WO2009001108 | 12/2008 |
| WO | WO2009006615 | 1/2009 |
| WO | WO2009029453 | 3/2009 |
| WO | WO 2009031149 | 3/2009 |
| WO | WO2009036334 | 3/2009 |
| WO | WO2009051829 | 4/2009 |
| WO | WO2009051830 | 4/2009 |
| WO | WO2009063377 | 5/2009 |
| WO | WO2009081348 | 7/2009 |
| WO | WO2009111664 | 9/2009 |
| WO | WO2009146082 | 12/2009 |
| WO | WO0100085 | 1/2010 |
| WO | WO2010009100 | 1/2010 |
| WO | WO2010011833 | 1/2010 |
| WO | WO2010019778 | 2/2010 |
| WO | WO2010057049 | 5/2010 |
| WO | WO2010080765 | 7/2010 |
| WO | WO2010080843 | 7/2010 |
| WO | WO2010107563 | 9/2010 |
| WO | WO2010129288 | 11/2010 |
| WO | WO2010132331 | 11/2010 |
| WO | WO2010135516 | 11/2010 |
| WO | WO2011068963 | 6/2011 |
| WO | WO2011133799 | 10/2011 |
| WO | WO2011159336 | 12/2011 |
| WO | WO2011159337 | 12/2011 |
| WO | WO2011159338 | 12/2011 |
| WO | WO2011159339 | 12/2011 |
| WO | WO2015112603 | 7/2015 |
| WO | WO2015112604 | 7/2015 |
| WO | WO2015119911 | 8/2015 |

OTHER PUBLICATIONS

Arshak et al., A Review and Adaptation of Methods of Object Tracking to Telemetry Capsules IC-Med (2007) vol. 1, No. 1, Issue 1, 12pp.

"ASGE Technology Status Evaluation Report: wireless capsule endoscopy" American Soc. for Gastrointestinal Endoscopy (2006) vol. 63, No. 4; 7 pp.

Aydin et al., "Design and implementation considerations for an advanced wireless interface in miniaturized integrated sensor Microsystems" Sch. of Eng. & Electron., Edinburgh Univ., UK; (2003); abstract.

Barrie, Heidelberg pH capsule gastric analysis. Texbook of Natural Medicine, (1992), Pizzorno, Murray & Barrie.

Bohidar et al., "Dielectric Behavior of Gelatin Solutions and Gels" Colloid Polym Sci (1998) 276:81-86.

Brock, "Smart Medicine: The Application of Auto-ID Technology to Healthcare" Auto-ID Labs (2002) http://www.autoidlabs.org/uploads/media/MIT-AUTOID-WH-010.pdf.

Carlson et al., "Evaluation of a non-invasive respiratory monitoring system for sleeping subjects" Physiological Measurement (1999) 20(1): 53.

Coury, L. "Conductance Measurement Part 1: Theory"; Current Separations, 18:3 (1999) p. 91-96.

Delvaux et al., "Capsule endoscopy: Technique and indications" Clinical Gastroenterology (2008) vol. 22, Issue 5, pp. 813-837.

Dhar et al., "Electroless nickel plated contacts on porous silicon" Appl. Phys. Lett. 68 (10) pp. 1392-1393 (1996).

Eldek A., "Design of double dipole antenna with enhanced usable bandwidth for wideband phased array applications" Progress in Electromagnetics Research PIER 59, 1-15 (2006).

Fawaz et al., "Enhanced Telemetry System using CP-QPSK Band—Pass Modulation Technique Suitable for Smart Pill Medical Application" IFIP IEEE Dubai Conference (2008); http://www.asic.fh-offenburg.de/downloads/ePille/IFIP_IEEE_Dubai_Conference.pdf.

Ferguson et al., "Dialectric Constant Studies III Aqueous Gelatin Solutions" J. Chem. Phys. 2, 94 (1934) p. 94-98.

Furse C. M., "Dipole Antennas" J. Webster (ed). Wiley Encyclopedia of Electrical and Electronics Engineering (1999) p. 575-581.

Gaglani S. "Put Your Phone, or Skin, on Vibrate" MedGadget (2012) http://medgadget.com/2012/03/put-your-phone-or-skin-on-vibrate.html 8pp.

Gilson, D.R. "Molecular dynamics simulation of dipole interactions", Department of Physics, Hull University, Dec. 2002, p. 1-43.

Given Imaging, "Agile Patency Brochure" (2006) http://www.inclino.no/documents/AgilePatencyBrochure_Global_GMB-0118-01.pdf; 4pp.

Gonzalez-Guillaumin et al., "Ingestible capsule for impedance and pH monitoring in the esophagus" IEEE Trans Biomed Eng. (2007) 54(12): 2231-6; abstract.

Greene, "Edible RFID microchip monitor can tell if you take your medicine" Bloomberg Businessweek (2010) 2 pp.; http://www.businessweek.com/idg/2010-03-31/edible-rfid-microchip-monitor-can-tell-if-you-take-your-medicine.html.

Heydari et al., "Analysis of the PLL jitter due to power/ground and substrate noise"; IEEE Transactions on Circuits and Systems (2004) 51(12): 2404-16.

Hoeksma, J. "New 'smart pill' to track adherence" E-Health-Insider (2010) http://www.e-health-insider.com/news/5910/new_'smart_pill'_monitors_medicines.

Hoover et al., "Rx for health: Engineers design pill that signals it has been swallowed" University of Florida News (2010) 2pp.; http://news.ufl.edu/2010/03/31/antenna-pill-2/.

Intromedic, MicroCam Innovative Capsule Endoscope Pamphlet. (2006) 8 pp (http://www.intromedic.com/en/product/productinfo.asp).

ISFET—Ion Sensitive Field-Effect Transistor; Microsens S.A. pdf document. Office Action dated Jun. 13, 2011 for U.S. Appl. No. 12/238,345; 4pp.

(56) References Cited

OTHER PUBLICATIONS

Jung, S. "Dissolvable Transient Electronics' Will Be Good for Your Body and the Environment" MedGadget; Oct. 1, 2012; Onlne website: http://medgadget.com/2012/10/dissolvable-transient-electronics-will-be-good-for-your-body-and-the-environment.html; downloaded Oct. 24, 2012; 4 pp.
Juvenile Diabetes Research Foundation International (JDRF), "Artificial Pancreas Project" (2010); http://www.artificialpancreasproject.com/; 3 pp.
Kamada K., "Electrophoretic deposition assisted by soluble anode" Materials Letters 57 (2003) 2348-2351.
Kendle, Earl R. and Morris, Larry A., "Preliminary Studies in the Development of a Gastric Battery for Fish" (1964). Nebraska Game and Parks Commission White Papers, Conference Presentations, & Manuscripts. Paper 22. p. 1-6.
Kim et al., "A Semi-Interpenetrating Network System for a Polymer Membrane"; Eur. Polym. J. vol. 33 No. 7; pp. 1009-1014 (1997).
Li, P-Y, et al. "An electrochemical intraocular drug delivery device", Sensors and Actuators A 143 (2008) p. 41-48.
Lifescan, "OneTouch UltraLink™" http://www.lifescan.com/products/meters/ultralink (2010) 2 pp.
MacKay et al., "Radio Telemetering from within the Body" Inside Information is Revealed by Tiny Transmitters that can be Swallowed or Implanted in Man or Animal Science (1991) 1196-1202; 134; American Association for the Advancement of Science, Washington D.C.
MacKay et al., "Endoradiosonde" Nature, (1957) 1239-1240, 179 Nature Publishing Group.
McKenzie et al., "Validation of a new telemetric core temperature monitor" J. Therm. Biol. (2004) 29(7-8):605-11.
Medtronic, "CareLink Therapy Management Software for Diabetes" (2010); https://carelink.minimed.com/patient/entry.jsp?bhcp=1; 1 pp.
Medtronic, "Carelink™ USB" (2008) http://www.medtronicdiabetes.com/pdf/carelink_usb_factsheet.pdf 2pp.
Medtronic "The New MiniMed Paradigm® REAL-Time Revel™ System" (2010) http://www.medtronicdiabetes.com/products/index.html; 2 pp.
Medtronic, "MINI MED Paradigm® Revel™ Insulin Pump" (2010) http://www.medtronicdiabetes.com/products/insulinpumps/index.html; 2 pp.
Medtronic, Mini Med Paradigm™ Veo™ System: Factsheet (2010). http://www.medtronic-diabetes.com.au/downloads/Paradigm%20Veo%20Factsheet.pdf ; 4 pp.
Melanson, "Walkers swallow RFID pills for science" Engadget (2008); http://www.engadget.com/2008/07/29/walkers-swallow-rfid-pills-for-science/.
Minimitter Co. Inc. "Actiheart" Traditional 510(k) Summary. Sep. 27, 2005.
MiniMitter Co. Inc. Noninvasive technology to help your studies succeed. Mini Mitter.com Mar. 31, 2009.
Mini Mitter Co, Inc. 510(k) Premarket Notification Mini-Logger for Diagnostic Spirometer. 9-21 (1999).
Mini Mitter Co, Inc. 510(k) Premarket Notification for VitalSense. Apr. 22, 2004.
MiniMitter Co. Inc. VitalSense Integrated Physiological Monitoring System. Product Description. (2005).
MiniMitter Co. Inc. VitalSense Wireless Vital Signs Monitoring. Temperatures.com Mar. 31, 2009.
Mojaverian et al., "Estimation of gastric residence time of the Heidelberg capsule in humans: effect of varying food composition" Gastroenterology (1985) 89:(2): 392-7.
O'Brien et al., "The Production and Characterization of Chemically Reactive Porous Coatings of Zirconium Via Unbalanced Magnetron Sputtering" Surface and Coatings Technology (1996) 86-87; 200-206.
Park, "Medtronic to Buy MiniMed for $3.7 Billion" (2001) HomeCare; http://homecaremag.com/mag/medical_medtronic_buy_minimed/; 2 pp.
Radio Antennae, http://www.erikdeman.de/html/sail018h.htm; (2008) 5 pages.
"RFID "pill" monitors marchers" RFID News (2008) http://www.rfidnews.org/2008/07/23/rfid-pill-monitors-marchers/.
Rolison et al., "Electrically conductive oxide aerogels: new materials in electrochemistry" J. Mater. Chem. (2001) 1, 963-980.
Roulstone, et al., "Studies on Polymer Latex Films: I. A study of latex film morphology" Polymer International 24 (1991) pp. 87-94.
Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.
Santini, J.T. et al, "Microchips as controlled drug delivery-devices", Agnew. Chem. Int. Ed. (2000), vol. 39, p. 2396-2407.
"SensiVida minimally invasive clinical systems" Investor Presentation Oct. 2009 28pp; http://www.sensividamedtech.com/SensiVidaGeneralOctober09.pdf.
Shawgo, R.S. et al. "BioMEMS from drug delivery", Current Opinion in Solid State and Material Science 6 (2002), p. 329-334.
Shin et al., "A Simple Route to Metal Nanodots and Nanoporous Metal Films"; Nano Letters, vol. 2, No. 9 (2002) pp. 933-936.
Shrivas et al., "A New Platform for Bioelectronics-Electronic Pill", Cummins College, (2010).; http://www.cumminscollege.org/downloads/electronics_and_telecommunication/Newsletters/Current%20Newsletters.pdf; First cited in third party client search conducted by Patent Eagle Search May 18, 2010.
"Smartlife awarded patent for knitted transducer" Innovation in Textiles News: http://www.innovationintextiles.com/articles/208.php; 2pp. (2009).
"The SmartPill Wireless Motility Capsule" Smartpill, The Measure of GI Health; (2010) http://www.smartpillcorp.com/index.cfm?pagepath=Products/The_SmartPill_Capsule&id=17814.
Solanas et al., "RFID Technology for the Health Care Sector" Recent Patents on Electrical Engineering (2008) 1, 22-31.
Soper, S.A. et al. "Bio-Mems Technologies and Applications", Chapter 12, "MEMS for Drug Delivery", p. 325-346 (2007).
Swedberg, "University Team Sees Ingestible RFID Tag as a Boon to Clinical Trials" RFID Journal Apr. 27, 2010; http://www.rfidjournal.com/article/view/7560/1 3pp.
Tajalli et al., "Improving the power-delay performance in subthreshold source-coupled logic circuits" Integrated Circuit and System Design. Power and Timing Modeling, Optimization and Simulation, Springer Berlin Heidelberg (2008) 21-30.
Tatbul et al., "Confidence-based data management for personal area sensor networks" ACM International Conference Proceeding Series (2004) 72.
Tierney, M.J. et al "Electroreleasing Composite Membranes for Delivery of Insulin and other Biomacromolecules", J. Electrochem. Soc., vol. 137, No. 6, Jun. 1990, p. 2005-2006.
Trutag Technologies, Inc., Spectral Microtags for Authentication and Anti-Counterfeiting; "Product Authentication and Brand Protection Solutions"; http://www.trutags.com/; downloaded Feb. 12, 2013; 1 pp.
Walkey, "MOSFET Structure and Processing"; 97.398* Physical Electronics Lecture 20; 24 pp.
Watson, et al., "Determination of the relationship between the pH and conductivity of gastric juice" Physiol Meas. 17 (1996) pp. 21-27.
Whipple, Fred L.; "Endoradiosonde," Nature, Jun. 1957, 1239-1240.
Winter, J. et al. "The material properties of gelatin gels"; USA Ballistic Research Laboratories, Mar. 1975, p. 1-157.
Wongmanerod et al., "Determination of pore size distribution and surface area of thin porous silicon layers by spectroscopic ellipsometry" Applied Surface Science 172 (2001) 117-125.
Xiaoming et al., "A telemedicine system for wireless home healthcare based on bluetooth and the internet" Telemedicine Journal and e-health (2004) 10(S2): S110-6.
Yang et al., "Fast-switching frequency synthesizer with a discriminator-aided phase detector" IEEE Journal of Solid-State Circuits (2000) 35(10): 1445-52.
Yao et al., "Low Power Digital Communication in Implantable Devices Using Volume Conduction of Biological Tissues" Proceedings of the 28th IEEE, EMBS Annual International Conference, Aug. 30-Sep. 3, 2006.

(56) References Cited

OTHER PUBLICATIONS

Zimmerman, "Personal Area Networks: Near-field intrabody communication" IBM Systems Journal (1996) 35 (3-4):609-17.
Description of ePatch Technology Platform for ECG and EMG, located it http://www.madebydelta.com/imported/images/DELTA_Web/documents/ME/ePatch_ECG_EMG.pdf, Dated Sep. 2, 2010.
Zworkin, "A Radio Pill" Nature, (1957) 898, 179 Nature Publishing Group.
International Search Report for PCT/US2013/065041 dated Jan. 28, 2014 (3 pages).
International Preliminary Report on Patentability for PCT/US2013/065041 dated Apr. 21, 2015 (6 pages).
Philips Respironics Products, Noninvasive Technology to Help Your Studies Succeed. 510 (k) Permanent Notification for Vital Sense. Apr. 22, 2004; http/minimitter.com/products.cfm.
Wang, X. et al "Resistance to Tracking and Erosion of Silicone Rubber Material under Various Types of Precipitation", Jpn. J. Appl. Phys. vol. 38 (1999) pp. 5170-5175.

* cited by examiner

APPARATUS, SYSTEM, AND METHOD TO ADAPTIVELY OPTIMIZE POWER DISSIPATION AND BROADCAST POWER IN A POWER SOURCE FOR A COMMUNICATION DEVICE

This application claims priority to International Application No. PCT/US2013/065041 filed Oct. 15, 2013, which application, pursuant to 35 U.S.C. §119 (e), claims priority to the filing date of U.S. Provisional Patent Application Ser. No. 61/715,610 filed Oct. 18, 2012; the disclosures of which are herein incorporated by reference.

INTRODUCTION

The present disclosure is directed generally to techniques to adaptively optimize power dissipation and broadcast power in a power source for a communication device. More particularly, the present disclosure is directed to techniques to adaptively optimize power dissipation and broadcast power in a power source for an ingestible communication device. In particular, the present disclosure is directed to techniques to adaptively optimize power dissipation or adaptively optimize broadcast power for an ingestible event marker (IEM) (or a combination thereof), which acts as a galvanic electrical power source, e.g., battery, while dissimilar materials dissolve when exposed to a conducting fluid. Once energized in the manner discussed herein, the IEM communicates a broadcast signal, as described in more detail hereinbelow. Accordingly, it may be desirable, during an IEM broadcast cycle, to optimize transmission of signals while minimizing the charge removed from the galvanic battery source. It may be further desirable to optimize signal transmission by controlling the combination of current drained from the battery and the pulse width of a transmission pulse during the broadcast cycle and balancing the output charge against a pre-determined battery recovery voltage or battery impedance measurement.

The present disclosure also is directed generally to an apparatus, system, and method to determine the availability of battery power prior to the ingestible communication device entering a high current draw mode of operation. For ingestible device, such as IEM, operations, where the battery impedance is determined by the amount of material dissolution over time, and could vary by a factor of ten or more, it may be desirable to know that the battery is capable of sustaining a predetermined current draw prior to performing broadcast communication operations.

The present disclosure also is directed generally to an apparatus, system, and method for integrated circuits using the substrate as a negative terminal. It is not uncommon for complementary metal oxide semiconductor (CMOS) devices using P type starting material to have their substrate referenced to the most negative potential of the system. For an ingestible device, such as IEM, this substrate connection forms the negative terminal of the power source, while the top of the semiconductor wafer is connected to the positive terminal of the power source. Given this configuration, it may be difficult to provide a negative terminal connection on the top side of the wafer due to the possibility of either shorting the positive terminal during power source activation, or causing increased leakage currents between the two terminals. This difficulty in providing a negative terminal on the top side of the wafer and relying on the substrate connection only, may cause measurement inaccuracies at wafer sort test due to the impedance from the substrate to the on chip circuits connected to the negative terminal. Accordingly, it may be desirable to provide a negative terminal connection that can be placed on the top side of the wafer that is activated only during test modes and is left in a high impedance state during all other modes of operation.

The present disclosure also is directed generally to an apparatus, system, and method to separate a power source from a broadcast power source in an ingestible device, such as an IEM. In a typical architecture, the power source of an IEM is shared between the digital circuits, analog circuits and I/O circuits. This sharing of the power source results in additional circuitry of which is required to disconnect the shared power source from the analog and/or digital circuits prior to broadcast as to not affect their operation and store enough charge on storage device so that the analog and digital circuits remain operational during the time the power source is disconnected from these circuits. Accordingly, it may be desirable to provide a method whereby the IEM power source can be physically separated into multiple power sources of predetermined values allowing the removal of the charge storage device. In addition, it may be desirable to provide an architecture to de-sensitize the digital and analog circuits from any coupling effect that the close proximity of one power source to another may cause.

SUMMARY

In one aspect, a method of stabilizing battery voltage of a battery device while optimizing power delivered to a receiver during communication of a broadcast packet is provided. The method comprises receiving, by a logic circuit, a broadcast packet having a predetermined number of bits for communication by a controller to a receiver located remotely from the controller; determining, by the logic circuit, a number of cycles in which a sampled battery voltage is either greater than or less than or equal to a nominal battery voltage over a first subset of the predetermined number of bits of the broadcast packet; and performing, by the logic circuit, either a tune-up or tune-down procedure based on the number of cycles counted in which the sampled battery voltage is not equal to the nominal battery voltage for more than one half of a total number of cycles counted.

FIGURES

DESCRIPTION

Before explaining various aspects of apparatuses, systems, and methods for adaptively optimizing power dissipation and broadcast power in a power source for a communication device in detail, it should be noted that the aspects of such techniques disclosed herein are not limited in application or use to the details of construction and arrangement of parts illustrated in the following description and accompanying drawings. The various aspects may be implemented or incorporated in other aspects, variations and modifications, and may be practiced or carried out in various ways. Further, unless otherwise indicated, the terms and expressions employed herein have been chosen for the purpose of describing the illustrative aspects for the convenience of the reader and are not for the purpose of limitation thereof. Further, it should be understood that any one or more of the disclosed aspects, expressions thereof, and examples, can be combined with any one or more of the other disclosed aspects, expressions thereof, and examples, without limitation.

Embodiment 1

In one aspect, the present disclosure is directed generally to an apparatus, system, and method for adaptively optimizing power dissipation and broadcast power in a power source, such as a battery, for a communication device. More particularly, in one aspect, the present disclosure is directed to an apparatus, system, and method for adaptively optimizing power dissipation and broadcast power in a power source for an ingestible communication device. More particularly, in yet another aspect, the present disclosure is directed to an apparatus, system, and method for adaptively optimizing power dissipation and broadcast power in a battery for an IEM, for example.

In one aspect techniques for adaptively optimizing power dissipation and broadcast power in a power source, such as a battery, for a communication device may be implemented with automatic calibration decision logic employing tune-up and tune-down procedures for adaptively optimizing power dissipation and broadcast power in a battery. In accordance with the present disclosure, the automatic calibration decision logic, including tune-up and tune-down procedures for adaptively optimizing power dissipation and broadcast power in a battery can be practiced, is implemented in a system comprising an IEM. Aspects of IEM devices are disclosed in U.S. Pat. No. 7,978,064 to Zdeblick et al., titled "Communication System with Partial Power Source," which is incorporated herein by reference in its entirety.

Before describing various aspects of the automatic calibration decision logic and tune-up/tune-down procedures for adaptively optimizing power dissipation and broadcast power in a battery, the present disclosure now turns to a brief description of a system in which the automatic calibration decision logic and tune-up/tune-down procedures for adaptively optimizing power dissipation and broadcast power in a battery can be practiced.

Figure 1:
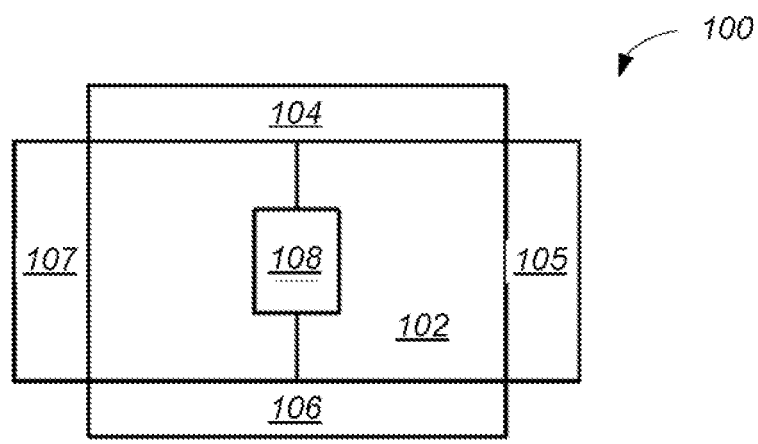
FIG. 1 is a block diagram representation of one aspect of an event indicator system with dissimilar metals positioned on opposite ends.

Accordingly, FIG. 1 is a block diagram representation of one aspect of an event indicator system 100 with dissimilar metals positioned on opposite ends. In one aspect, the system 100 can be used in association with any pharmaceutical product. In one aspect, the system, may be used to determine when a patient takes the pharmaceutical product, such as a pill, tablet, or capsule, without limitation. The scope of the present disclosure, however, is not limited by the environment and the product that is used with the system 100. For example, the system 100 may be placed on a tablet or within a capsule and placed within a conducting liquid. The tablet or capsule would then dissolve over a period of time and release the system 100 into the conducting liquid. Thus, in one aspect, the tablet or capsule may contain the system 100 without a pharmaceutical agent or product. Such a capsule, for example, may be used in any environment where a conducting liquid is present and with any product, such as an active pharmaceutical agent, vitamin, placebo, without limitation. In various examples, the capsule or tablet may be dropped into a container filled with jet fuel, salt water, tomato sauce, motor oil, or any similar product. Additionally, the capsule containing the system 100 may be ingested at the same time that a pharmaceutical product is ingested in order to record the occurrence of the event, such as when the product was taken or to trigger any other event.

In the specific example of the system 100 combined with the pharmaceutical product, as the product or pill is ingested, the system 100 is activated. The system 100 controls conductance to produce a unique current signature that is detected, thereby signifying that the pharmaceutical product has been taken. The system 100 includes a framework 102. The framework 102 is a chassis for the system 100 and multiple components are attached to, deposited upon, or secured to the framework 102. In this aspect of the system 100, a digestible first material 104 is physically associated with the framework 102. The material 104 may be chemically deposited on, evaporated onto, secured to, or built-up on the framework all of which may be referred to herein as "deposit" with respect to the framework 102. The material 104 is deposited on one side of the framework 102. The materials of interest that can be used as material 104 include, but are not limited to: Cu or CuI. The material 104 is deposited by physical vapor deposition, electrodeposition, or plasma deposition, among other protocols. The material 104 may be from about 0.05 to about 500 µm thick, such as from about 5 to about 100 µm thick. The shape is controlled by shadow mask deposition, or photolithography and etching. Additionally, even though only one region is shown for depositing the material, each system 100 may contain two or more electrically unique regions where the material 104 may be deposited, as desired.

At a different side, which may be the opposite side as shown in FIG. 1, a digestible second material 106 is deposited, such that the materials 104 and 106 are dissimilar. Although not shown, the different side selected may be the side next to the side selected for the material 104. The scope of the present invention is not limited by the side selected and the term "different side" can mean any of the multiple sides that are different from the first selected side. Furthermore, even though the shape of the system is shown as a square, the shape may be any geometrically suitable shape. The first and second materials 104, 106 are selected such that they produce a voltage potential difference when the system 100 is in contact with conducting liquid, such as body fluids. The materials of interest for material 106 include, but are not limited to: Mg, Zn, or other electronegative metals. As indicated above with respect to the first material 104, the second material 106 may be chemically deposited on, evaporated onto, secured to, or built-up on the framework. Also, an adhesion layer may be necessary to help the second material 106 (as well as the first material 104 when needed) to adhere to the framework 102. Typical adhesion layers for the second material 106 are Ti, TiW, Cr or similar material. Anode material and the adhesion layer may be deposited by physical vapor deposition, electrodeposition or plasma deposition. The second material 106 may be from about 0.05 to about 500 μm thick, such as from about 5 to about 100 μm thick. However, the scope of the present invention is not limited by the thickness of any of the materials nor by the type of process used to deposit or secure the materials to the framework 102.

According to the disclosure set forth, the materials 104, 106 can be any pair of materials with different electrochemical potentials. Additionally, in the embodiments wherein the system 100 is used in-vivo, the materials 104, 106 may be vitamins that can be absorbed. More specifically, the materials 104, 106 can be made of any two materials appropriate for the environment in which the system 100 will be operating. For example, when used with an ingestible product, the materials 104, 106 are any pair of materials with different electrochemical potentials that are ingestible. An illustrative example includes the instance when the system 100 is in contact with an ionic solution, such as stomach acids. Suitable materials are not restricted to metals, and in certain embodiments the paired materials are chosen from metals and non-metals, e.g., a pair made up of a metal (such as Mg) and a salt (such as CuCl or CuI). With respect to the active electrode materials, any pairing of substances—metals, salts, or intercalation compounds—with suitably different electrochemical potentials (voltage) and low interfacial resistance are suitable.

Materials and pairings of interest include, but are not limited to, those reported in Table 1 below. In one aspect, one or both of the metals may be doped with a non-metal, e.g., to enhance the voltage potential created between the materials as they come into contact with a conducting liquid. Non-metals that may be used as doping agents in certain embodiments include, but are not limited to: sulfur, iodine and the like. In another embodiment, the materials are copper iodine (CuI) as the anode and magnesium (Mg) as the cathode. Aspects of the present disclosure use electrode materials that are not harmful to the human body.

TABLE 1

| | Anode | Cathode |
|---|---|---|
| Metals | Magnesium, Zinc Sodium (†), Lithium (†) Iron | |
| Salts | | Copper salts: iodide, chloride, bromide, sulfate, formate, (other anions possible) $Fe^{3+}$ salts: e.g. orthophosphate, pyrophosphate, (other anions possible) Oxygen (††) on platinum, gold or other catalytic surfaces |
| Intercalation compounds | Graphite with Li, K, Ca, Na, Mg | Vanadium oxide Manganese oxide |

Thus, when the system 100 is in contact with the conducting liquid, a current path, is formed through the conducting liquid between the first and second materials 104, 106. A controller 108 is secured to the framework 102 and electrically coupled to the first and second materials 104, 106. The controller 108 includes electronic circuitry, for example control logic that is capable of controlling and altering the conductance between the materials 104, 106.

The voltage potential created between the first and second materials 104, 106 provides the power for operating the system 100 as well as produces the current flow through the conducting fluid and the system. In one aspect, the system 100 operates in direct current mode. In an alternative aspect, the system 100 controls the direction of the current so that the direction of current is reversed in a cyclic manner, similar to alternating current. As the system 100 reaches the conducting fluid or the electrolyte, where the fluid or electrolyte component is provided by a physiological fluid, e.g., stomach acid, the path for current flow between the materials 104, 106 is completed external to the system 100; the current path through the system 100 is controlled by the controller 108. Completion of the current path allows for the current to flow and in turn a receiver 304 (shown in FIG. 3), can detect the presence of the current and receive the information transmitted/radiated by the system 100. In one aspect, the receiver recognizes that the system 100 has been activated and the desired event is occurring or has occurred.

In one aspect, the two materials 104, 106 may be similar in function to the two electrodes needed for a direct current power source, such as a battery. The conducting liquid acts as the electrolyte needed to complete the power source. The completed power source described is defined by the physical chemical reaction between the materials 104, 106 of the system 100 and the surrounding fluids of the body. The completed power source may be viewed as a power source that exploits reverse electrolysis in an ionic or a conductive solution such as gastric fluid, blood, or other bodily fluids and some tissues. Additionally, the environment may be something other than a body and the liquid may be any conducting liquid. For example, the conducting fluid may be salt water or a metallic based paint.

In certain aspects, the two materials 104, 106 may be shielded from the surrounding environment by an additional layer of material. Accordingly, when the shield is dissolved and the two dissimilar materials 104, 106 are exposed to the target site, a voltage potential is generated.

In certain aspects, the complete power source or supply is one that is made up of active electrode materials, electrolytes, and inactive materials, such as current collectors, packaging, etc. The active materials are any pair of materials with different electrochemical potentials. Suitable materials are not restricted to metals, and in certain embodiments the paired materials are chosen from metals and non-metals, e.g., a pair made up of a metal (such as Mg) and a salt (such as CuI). With respect to the active electrode materials, any pairing of substances—metals, salts, or intercalation compounds—with suitably different electrochemical potentials (voltage) and low interfacial resistance are suitable.

A variety of different materials may be employed as the materials that form the electrodes. In certain aspects, electrode materials are chosen to provide for a voltage upon contact with the target physiological site, e.g., the stomach, sufficient to drive the system of the identifier. In certain embodiments, the voltage provided by the electrode materials upon contact of the metals of the power source with the target physiological site is 0.001 V or higher, including 0.01 V or higher, such as 0.1 V or higher, e.g., 0.3 V or higher, including 0.5 volts or higher, and including 1.0 volts or higher, where in certain embodiments, the voltage ranges from about 0.001 to about 10 volts, such as from about 0.01 to about 10 V.

The first and second materials 104, 106 provide the voltage potential to activate the control device 108. Once the control device 108 is activated or powered up, the control device 108 can alter conductance between the materials 104, 106 in a unique manner. By altering the conductance between materials 104, 106, the control device 108 is capable of controlling the magnitude and the duty cycle of the current through the conducting liquid that surrounds the system 100. This produces a unique current signature that can be detected and measured by the receiver 304 (shown in FIG. 3), which can be positioned internal or external to the body. Information can be communicated by the system 100 in the form of packets until the first and second materials can no longer sustain the power source. In addition to controlling the magnitude of the current path between the materials, non-conducting materials, membrane, or "skirt" are used to increase the "length" of the current path and, hence, act to boost the conductance path, as disclosed in the U.S. patent application Ser. No. 12/238,345 entitled, "In-Body Device with Virtual Dipole Signal Amplification" filed Sep. 25, 2008, the entire content of which is incorporated herein by reference. Alternatively, throughout the disclosure herein, the terms "non-conducting material," "membrane," and "skirt" are interchangeably with the term "current path extender" without impacting the scope or the present embodiments and the claims herein. The skirt elements 105, 107 may be associated with, e.g., secured to, the framework 102. Various shapes and configurations for the skirt are contemplated as within the scope of the present invention. For example, the system 100 may be surrounded entirely or partially by the skirt and the skirt maybe positioned along a central axis of the system 100 or off-center relative to a central axis. Thus, the scope of the present disclosure as claimed herein is not limited by the shape or size of the skirt. Furthermore, in other embodiments, the first and second materials 104, 106 may be separated by one skirt that is positioned in any defined region between the materials 104, 106.

Figure 2:
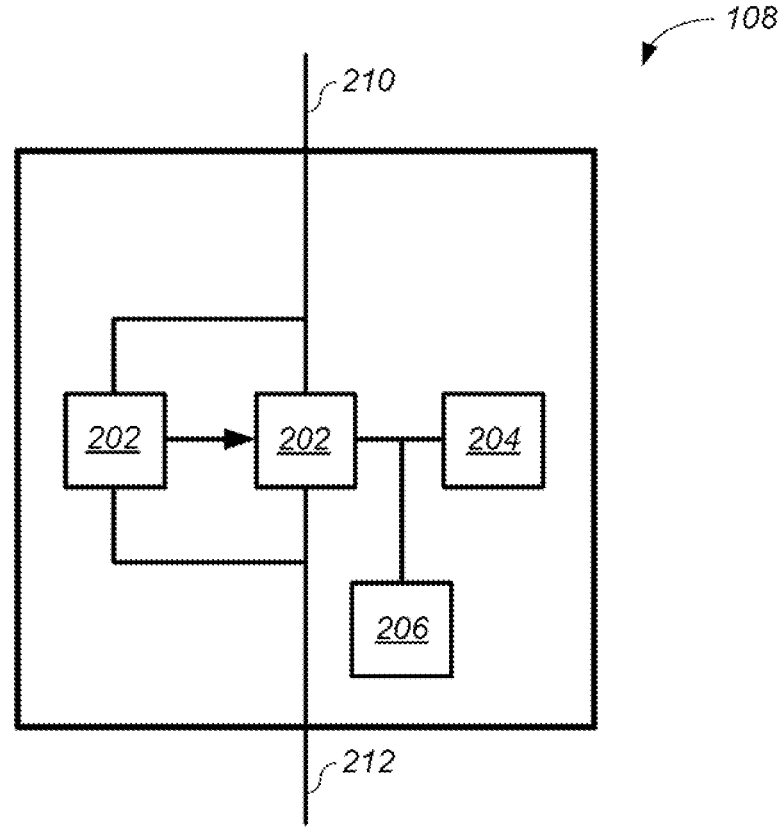
FIG. 2 is a block diagram illustration of one aspect of a control device used that may be employed in the system of FIG. 1.

Referring now to FIG. 2, a block diagram representation of the controller 108 is shown. The device 108 includes a control module 202, a counter or clock 204, a memory 206, and a logic circuit 208. Additionally, the controller 108 may include one or more sensor modules. The control module 202 has an input 210 electrically coupled to the first material 104 and an output 212 electrically coupled to the second material 106. The control module 202, the clock 204, the memory 206, and the logic circuit 208 (and optionally the sensor modules) also have power inputs (some not shown). The power for each of these components is supplied by the voltage potential produced by the chemical reaction between the first and second materials 104, 106 and the conducting fluid, when the system 100 is in contact with the conducting fluid. The control module 202 controls the conductance through logic that alters the overall impedance of the system 100. The control module 202 is electrically coupled to the clock 204. The clock 204 provides a clock cycle to the control module 202. Based upon the programmed characteristics of the control module 202, when a set number of clock cycles have passed, the control module 202 alters the conductance characteristics between the first and second materials 104, 106. This cycle is repeated and thereby the controller 108 produces a unique current signature characteristic. The control module 202 is also electrically coupled to the memory 206. Both the clock 204 and the memory 206 are powered by the voltage potential created between the first and second materials 104, 106.

Figure 3:
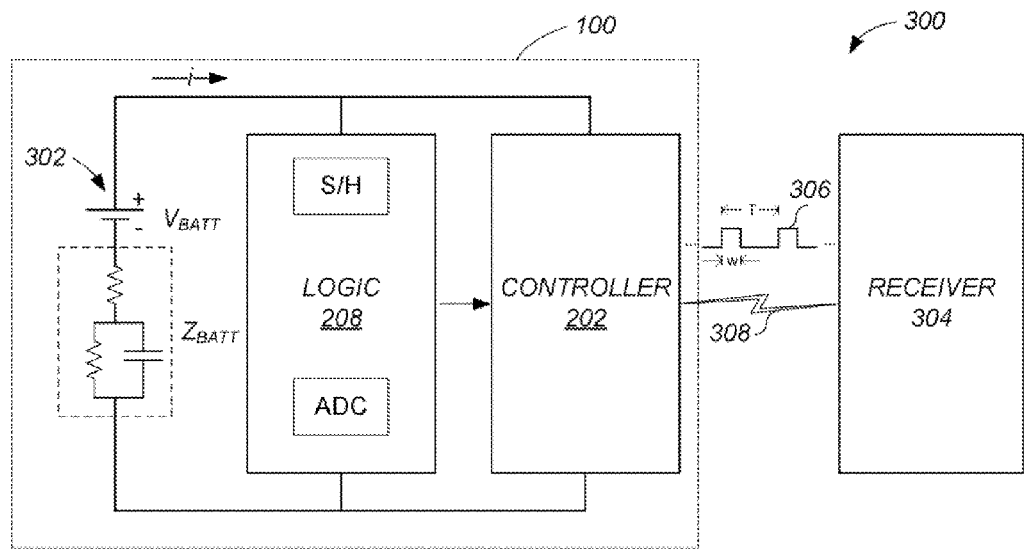
FIG. 3 is a block diagram of one aspect of an event indicator system in communication with a receiver.

As shown in FIG. 3, in one aspect, a logic circuit 208 is provided to monitor the current drain and impedance of the resulting power source or battery formed between the first and second materials when the system is immersed in an ionic fluid. In one aspect, the logic circuit 208, comprising a sample-and-hold and an analog-to-digital converter (ADC), is configured as an automatic calibration algorithm or process to adaptively optimize power dissipation and broadcast power in the resulting power source. In one aspect, and described in more detail hereinbelow, the logic circuit 208 monitors and adjusts the pulse width and current limit of the output of the system 100 in order to stabilize the battery voltage and the duty cycle of the transmitted signal, while optimizing the power delivered to the receiver 304 (shown in FIG. 3). In one aspect, the algorithm may be implemented to sample the value of the battery voltage ($V_{BATT}$) during the transmission of a predetermined data packet. In one aspect, adjustments to the pulse width and/or current limit may take effect during the transmission of a subsequent packet, such as, for example, during the transmission of the next data packet. The algorithm settings (starting pulse width, minimum and maximum current limits) may be programmed into the memory 206, such as a non-volatile memory, for example. This programming step may be performed, for example, at the wafer sort stage. In operation, the logic circuit 208 may execute a tune-up or tune-down procedure depending on the state of the battery recovery voltage and battery impedance. The logic circuit 208, including the tune-up and tune-down procedures, is described in more detail hereinbelow with reference to FIGS. 5-7. The logic circuit 208 may be implemented in hardware, software, or a combination thereof. In one aspect, the logic circuit 208 may be implemented either as a processor, state machine, digital signal processor, discrete logic among other implementations, which would be readily apparent to one of ordinary skill in the art. In one aspect, the logic circuit 208 may be embodied in an application specific integrated circuit (ASIC). Thus, the use of the term algorithm or procedure should not necessarily be interpreted as the execution of computer instructions. In one aspect, the logic circuit 208 is powered by the voltage potential created between the first and second materials 104, 106.

FIG. 3 is a block diagram of one aspect of a communication system 300 where an event indicator system 100 is in communication with a receiver 304 over communication link 308. It will be appreciated that the communication link 308 can be a current flow produced by ionic emission or a wireless link, without limitation. In one aspect, the logic circuit 208 is coupled to a battery 302 power source, which is modeled as a voltage source $V_{BATT}$ having an internal impedance $Z_{BATT}$ and output current (i). The logic circuit 208 monitors the output current (i) of the battery 302 and the impedance $Z_{BATT}$ of the battery 302. In one aspect, the battery 302 is formed when the first and second materials 104, 106 are immersed in an ionic fluid as described in connection with FIGS. 1 and 2. Aspects of a receiver 304 device are disclosed in U.S. Pat. No. 8,114,021 to Robertson et al., titled "Body-associated Receiver and Method," which is incorporated herein by reference in its entirety.

In one aspect, the logic circuit 208 is configured to execute an automatic calibration algorithm or process to adaptively optimize power dissipation and broadcast power of the event indicator system 100. In one aspect, the controller 202 of the event indicator system 100 outputs a broadcast signal 306 to the receiver 304. The broadcast signal 306 is comprised of a sequence of pulses transmitted at a predetermined frequency (f). The individual pulses of the broadcast signal 306 define a bit of information and a sequence of pulses defines a packet of information. The pulses have a period (T) and a pulse width (w) during which time the output signal is active. The inverse of the pulse period (T) is the frequency of the broadcast signal 306. The pulses may be transmitted at a predetermined duty cycle, which is defined as the ratio of the pulse width (w) and the period (T).

$f = 1/T$ Hz

Duty Cycle = $w/T$

In one aspect, the controller 202 may transmit a broadcast signal 306 comprising a first packet of information, where the first packet comprises a predetermined number of pulses m (e.g., m bits of information) at a first frequency $f_1$. In one aspect, the controller 202 may transmit multiple first packets comprising the predetermined number of bits at the first frequency $f_1$. At some time later, the controller 202 may start broadcasting a second packet of information, where the second packet comprises a predetermined number of pulses n (e.g., n bits of information) at a second frequency $f_2$. In one aspect, the series of first packets at $f_1$ are broadcast to the receiver 304 at just enough power to wake up the receiver 304. The actual data or information associated with the event indicator system 100 is broadcast via the second aeries of packets at $f_2$. Thus, once the receiver 304 detects the first packets, it prepares to receive the data broadcast via the second packets.

The first frequency $f_1$ may be any predetermined frequency and in one aspect may be any frequency from about 10 to about 30 kHz and more preferably about 20 kHz. The second frequency $f_2$ may be any predetermined frequency and in one aspect may be any frequency from about 10 to about 15 kHz and more preferably about 12½ kHz.

In one aspect, the event indicator system 100 may broadcast a predetermined number of packets, for example, three to six packets or more, at the first frequency $f_1$ to delay the broadcast time between a packet at the first frequency $f_1$ and a packet at the second frequency $f_2$, or by changing the time interval between packets to avoid transmission collisions. Likewise, in one aspect, the event indicator system 100 may broadcast a predetermined number of packets, for example, three to six packets or more, at the second frequency $f_2$ to avoid transmission collisions. It will be appreciated, however, that the number of repeated packet transmissions at first or second frequency $f_1$, $f_2$ may be determined statistically based on the number of event indicator systems 100 ingested by the patient.

In one aspect, as described in more detail hereinbelow, the logic circuit 208 monitors and adjusts the pulse width (w) of the controller 202 output and the current (i) limit of a broadcast signal 306 generated by the event indicator system 100 in order to stabilize the battery voltage $V_{BATT}$ and the duty cycle of the broadcast signal 306 pulses, while optimizing the power delivered to the receiver 304. In one aspect, the logic is configured to sample the battery voltage $V_{BATT}$ during the broadcast transmission of a predetermined data packet by the controller 202. In one aspect, adjustments to the pulse width (w) and/or current (i) limit may be determined for a current packet broadcast and may be applied to a subsequent packet, such as, for example, during the broadcast transmission of the next data packet. The algorithm settings such as, for example, starting pulse width ($w_o$), minimum current ($i_{min}$), and maximum current ($i_{max}$) limits may be programmed into the memory 206 (FIG. 2), such as a non-volatile memory, for example. This programming step may be performed, for example, at the wafer sort stage.

In one aspect the minimum current $i_{min}$ is about 1 mA and the maximum current $i_{max}$ is about 4 mA. In one aspect, the minimum duty cycle $DC_{min}$ is about 15% and the maximum duty cycle $DC_{max}$ is about 50%. These values are merely examples, and the present system should not be limited in this context.

In operation, the logic circuit 208 may execute a tune-up or tune-down procedure depending on the state of the battery 302 recovery voltage $V_{BATT}$ and impedance $Z_{BATT}$. The logic circuit 208, including the tune-up and tune-down procedures, is described in more detail hereinbelow with reference to FIGS. 5-7.

The logic circuit 208 may be implemented in hardware, software, or a combination thereof. In one aspect, the logic circuit 208 may be implemented either as a processor, digital signal processor, discrete logic, or state machine, among other implementations, which would be readily apparent to one of ordinary skill in the art. In one aspect, the logic circuit 208 may be embodied in an application specific integrated circuit (ASIC). Thus, the use of the term algorithm or procedure should not necessarily be interpreted as the execution of computer instructions.

Although the aspects illustrated in connection with FIGS. 1-3, the logic circuit 208 is described in connection with adaptively optimizing power dissipation and broadcast power in a power source created between the first and second materials 104 and 106, the logic circuit 208 is not limited in this context. For example, the logic circuit 208 may be configured to adaptively optimize power dissipation and broadcast power in any energy source, such as, a conventional battery.

The receiver 304 may further employ a beacon functionality module. In various aspects, a beacon switching module may employ one or more of the following: a beacon wakeup module, a beacon signal module, a wave/frequency module, a multiple frequency module, and a modulated signal module.

The beacon switching module may be associated with beacon communications, e.g., a beacon communication channel, a beacon protocol, etc. For the purpose of the present disclosure, beacons are typically signals sent by the controller 108 either as part of a message or to augment a message (sometimes referred to herein as "beacon signals"). The beacons may have well-defined characteristics, such as frequency. Beacons may be detected readily in noisy environments and may be used for a trigger to a sniff circuit, such as described below.

In one aspect, the beacon switching module may comprise the beacon wakeup module, having wakeup functionality. Wakeup functionality generally comprises the functionality to operate in high power modes only during specific times, e.g., short periods for specific purposes, to receive a signal, etc. An important consideration on a receiver portion of a system is that it be of low power. This feature may be advantageous in an implanted receiver, to provide for both small size and to preserve a long-functioning electrical supply from a battery. The beacon switching module enables these advantages by having the receiver operate in a high power mode for very limited periods of time. Short duty cycles of this kind can provide optimal system size and energy draw features.

In practice, the receiver 304 may "wake up" periodically, and at low energy consumption, to perform a "sniff function" via, for example, a sniff circuit. It is during this period that the receiver 304 detects the first packet at the first frequency $f_1$. For the purpose of the present application, the term "sniff function" generally refers to a short, low-power function to determine if a transmitter, e.g., the communication system 100, is present. If a communication system 100 broadcast signal 306 is detected by the sniff function, the receiver 304 may transition to a higher power communication decode mode. If a communication system 100 broadcast signal 306 is not present, the receiver 304 may return, e.g., immediately return, to sleep mode. In this manner, energy is conserved during relatively long periods when a transmitter signal is not present, while high-power capabilities remain available for efficient decode mode operations during the relatively few periods when a broadcast signal 306 is present. Several modes, and combination thereof, may be available for operating the sniff circuit. By matching the needs of a particular system to the sniff circuit configuration, an optimized system may be achieved.

Figure 4A:
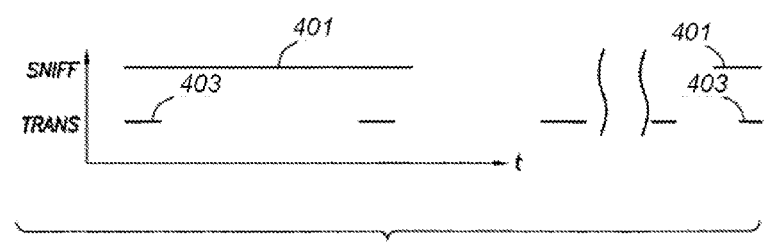
FIG. 4A illustrates one aspect of a beacon switching module providing a sniff period longer than a transmit signal repetition period.

FIG. 4A illustrates a diagram 400 where a beacon switching module wherein a sniff period 401 is longer than a broadcast signal 306 (FIG. 3) repetition period 403. The time function is provided on the horizontal axis. As shown, the broadcast signal 306 repeats periodically at a repetition period of 403, with a sniff function also running. In practice, effectively, the sniff period 401 may be longer than the broadcast signal 306 repetition period 403. In various aspects, there may be a relatively long period of time between the sniff periods. In this way, the sniff function, e.g., implemented as a sniff circuit, is guaranteed to have at least one transmission to occur each time the sniff circuit is active.

Figure 4B:
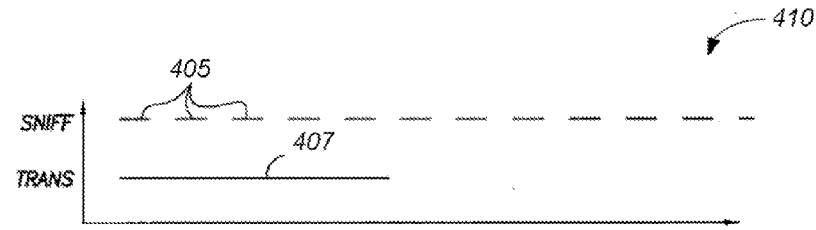
FIG. 4B illustrates one aspect of a beacon switching module providing a short but frequent sniff period and a long transmit packet are provided.

FIG. 4B illustrates a diagram 410 where the beacon switching module provides a short but frequent sniff period 405 and a long transmit packet 407 are provided. The sniff circuit will activate at some point during the transmit time. In this manner, the sniff circuit may detect the transmit signal and switch into a high power decode mode.

An additional beacon wakeup aspect is to provide the "sniffing" function in a continuous mode. This aspect of the transbody beacon transmission channel may exploit the fact that the total energy consumption is the product of average power consumption and time. In this aspect, the system may minimize the total energy consumption by having very short periods of activity, in which case the periods of activity are averaged down to a small number. Alternately, a low continuous sniff activity is provided. In this case, the configuration provides a sufficiently low power so that the transmission receiver runs continuously with total energy consumption at an appropriate level for the parameters of a specific system.

In one aspect, the sniff module of the receiver 304 is configured to scan for data encoded by the controller 202 in current flow produced by ionic emission. The data is received at the receiver 304 as a conductive signal at a set schedule, e.g., every 20 seconds. The period during active sniff is limited, e.g., 300 msec. This relatively low duty-cycle allows for lower average power functionality for extended system life. The receiver 304 determines if a broadcast signal 306 is present and if that broadcast signal 306 has a valid ID. If no signal having a valid ID is detected during active sniff, the active sniff is turned off until the next predetermined active period. If a broadcast signal 306 having a valid ID is received, the receiver 304 determines if the signal 306 received is from a previously detected ionic transmitter. If the broadcast signal 306 is from a previously detected ionic transmitter, the receiver 304 determines whether the count (in other words, individual valid detections of the same ID) in the current wake up cycle (specified time since the last reported ID, such as 10 minutes) is greater than a specified number (such as 50) as measured by a threshold counter. If the count exceeds this threshold as determined by the threshold counter the receiver 304 returns to sniff mode. If the count does not exceed the threshold value, the receiver operates in 100% detection mode to analyze the received data encoded in the current flow by the ionic emission. Once the received data is decoded and analyzed, the receiver 304 determines that the data encoded in the current flow is coming from a different valid source than previously detected, then the threshold counter is reset.

In another aspect, the incoming broadcast signal 306 to the receiver 304 represents the signals received by electrodes, bandpass filtered (such as from 10 KHz to 34 KHz) by a high frequency signaling chain (which encompasses the carrier frequency), and converted from analog to digital. The broadcast signal 306 is then decimated and mixed at the nominal drive frequency (such as, 12.5 KHz, 20 KHz, etc.) at a mixer. The resulting signal is decimated and low-pass filtered (such as 5 KHz BW) to produce the carrier signal mixed down to carrier offset-signal. The carrier offset-signal is further processed (fast Fourier transform and then detection of two strongest peaks) to provide the true carrier frequency signal. This protocol allows for accurate determination of the carrier frequency of the transmitted beacon.

Figure 5:
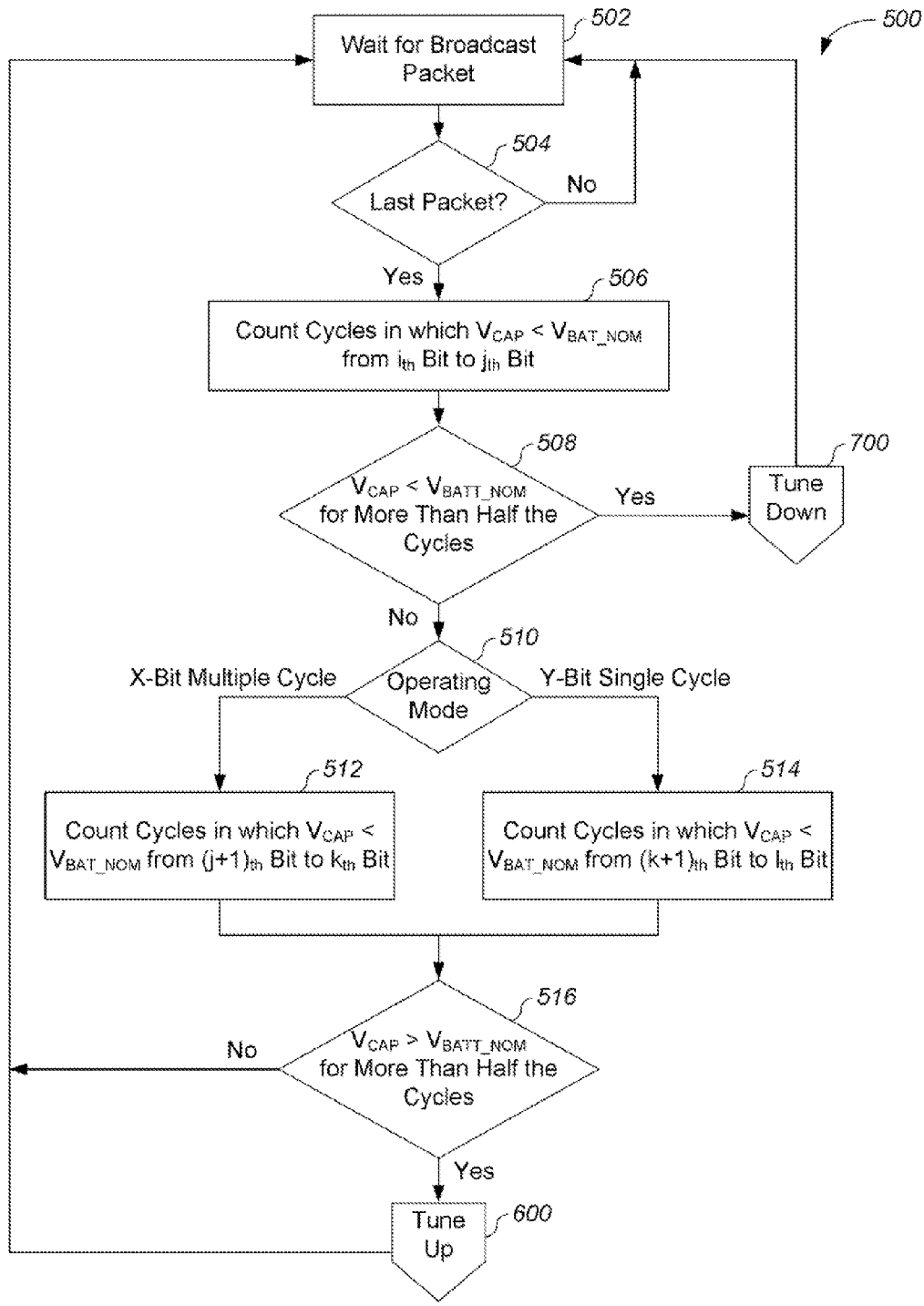
FIG. 5 illustrates one aspect of a decision logic for an automatic calibration process.

Having described in FIGS. 1-4, a general ingestible device system 100 in which the apparatus, system, and method to adaptively optimize power dissipation and broadcast power in a battery 302 may be practiced, the present disclosure now turns to a description of a flow diagram illustrating one aspect of a process for an automatic calibration decision logic 500 as shown in FIG. 5. The automatic calibration decision logic 500 can be implemented by the logic circuit 208. Accordingly, the automatic calibration decision logic 500 will be described with reference to FIGS. 1-5. During a broadcast cycle by the communication system 100, it is desirable to optimize the broadcast signal 306 while minimizing the charge removed from the battery 302 using one aspect of the procedure described in FIG. 5. The broadcast signal 306 may be optimized by controlling the combination of current (i) and pulse width (w) during a broadcast cycle, and balancing the output charge against a pre-determined battery 302 recovery voltage $V_{BATT-REC}$ or battery impedance $Z_{BATT}$ measurement.

In one aspect, this may be accomplished by a "tune-up" and "tune-down" process or algorithm as described in connection with FIGS. 6 and 7. During the tune-up phase the current (i) or pulse width (w) of the broadcast cycle is increased until the pre-determined battery 302 recovery voltage $V_{BATT-REC}$ or battery impedance $Z_{BATT}$ has been obtained. This step is then increased by one to ensure that the battery 302 voltage $V_{BATT}$ is greater than the battery 302 recovery voltage $V_{BATT-REC}$. The "tune-down" phase is then entered whereby the other parameter, current (i) or pulse width (w) of the broadcast cycle is decreased until the predetermined battery 302 recovery voltage $V_{BATT-REC}$ or battery impedance $Z_{BATT}$ is once again detected. This combination of broadcast current (i) and pulse width (w) is then stored in memory and used during a single broadcast cycle of a subsequent packet, e.g., the next packet.

In one aspect, the process of determining the battery 302 recovery voltage $V_{BATT-REC}$ or battery impedance $Z_{BATT}$ is accomplished by sampling the recovery voltage $V_{BATT-REC}$ of the battery 302 during a non broadcast cycle, and performing an average value calculation on the result. In addition, a starting value of current (i) and pulse width (w), as well as a maximum value of current (i) and pulse width (w) may be utilized by the optimization process to ensure that the minimum and maximum broadcast parameters are not violated.

During conventional transmission of broadcast signal 306, all the power of the battery 302 is exploited by essentially shorting the battery 302. This leads to a longer recovery time and faster discharge rate for the battery 302. In one aspect, the automatic calibration decision logic 500 provides a method for adaptively optimizing dissipation and broadcast power to extend the life of the battery 302 while still providing enough broadcast power to the controller 202 for suitable detection by the receiver 304. In one aspect, the automatic calibration decision logic 500 may be implemented by the logic circuit 208. Accordingly, with reference now to FIG. 5, one aspect of an automatic calibration decision logic 500. In one aspect, the automatic calibration decision logic 500 may be employed to adjust the pulse width (w) and current (i) limit of the broadcast signal 306 output by the controller 202 in order to stabilize the battery voltage $V_{BATT}$ and the duty cycle of the broadcast signal 306, while optimizing the power delivered to the receiver 304. In one aspect, the logic 500, samples the value of $V_{BATT}$ during a data packet transmission. In one aspect, the data packet transmission may be a 20 kHz data packet. Adjustments to the pulse width (w) and/or current (i) limit take effect starting with a subsequent data packet, such as, for example, the next data packet. In one aspect, the logic 500 settings (starting pulse width, minimum and maximum current limit) are programmable in the non-volatile memory 206 (FIG. 2) at wafer sort.

With reference now to FIGS. 3 and 5, at 502, the automatic calibration decision logic 500, e.g., the logic circuit 208, waits for the next available broadcast packet in order to characterize the battery voltage $V_{BATT}$ and impedance $Z_{BATT}$. At decision block 504, the logic circuit 208 determines whether the last broadcast packet is in the transmission queue. If no, the logic 500 process continues along the No branch and waits for the last packet. If yes, the logic 500 process continues along the Yes branch. At 506, the logic circuit 208 samples the battery 302 voltage $V_{BATT}$ and counts using a counter, e.g., determines, the number of cycles in which the sampled battery voltage ($V_{CAP}$) is less than a nominal battery voltage ($V_{BATT\_NOM}$), e.g., $V_{CAP}<V_{BATT\_NOM}$, from the $i_{th}$ bit to the $j_{th}$ bit of the broadcast packet. At decision block 508, the logic circuit 208 determines whether the sampled voltage $V_{CAP}$ is less than the nominal battery voltage $V_{BATT\_NOM}$ for more than half the cycles between the $i_{th}$ and $j_{th}$ bit of the broadcast packet. The sampled battery voltage ($V_{CAP}$) may be determined by the logic circuit 208 using, for example, the sample-and-hold circuit and an ADC, much like the sample-and-hold circuit 808 and analog-to-digital converter 812 shown and described in connection with FIG. 8, for example. Accordingly, in one aspect, the logic circuit 208 may be configured to employ internal or external sample-and-hold circuit and analog-to-digital converter circuits to sample the battery voltage.

When the sampled voltage $V_{CAP}$ is less than the nominal battery voltage $V_{BATT\_NOM}$ for more than half the cycles between the $i_{th}$ and $j_{th}$ bit of the broadcast packet, the logic 500 process continues along the Yes branch to the "tune-down" process 700, which is described in connection with FIG. 7. Briefly, during the "tune-down" 700 process, the current (i) or pulse width (w) of the broadcast cycle is decreased until the predetermined battery 302 recovery voltage $V_{BATT\text{-}REC}$ or battery impedance $Z_{BATT}$ is once again detected.

When the sampled voltage $V_{CAP}$ is less than the nominal battery voltage $V_{BATT\_NOM}$ for less than half the cycles between the $i_{th}$ and $j_{th}$ bit of the broadcast packet, the logic 500 process continues along the No branch to decision block 510 to determine the operating mode.

In one aspect, the logic 500 can be configured to operate on X-bit multiple cycle operating mode or a Y-bit single cycle operating mode. When operating in the X-bit multiple cycle mode, at 512 the logic circuit 208 count the number of cycles in which the sampled voltage is less than the nominal battery voltage, e.g., $V_{CAP}<V_{BAT\_NOM}$, from the $(j+1)_{th}$ bit to the $k_{th}$ bit. Otherwise, at 514 the logic circuit 208 counts the number of cycles in which $V_{CAP}<V_{BAT\_NOM}$ from the $(k+1)_{th}$ bit to the 6 bit. After counting such number of cycles, at decision block 516 the logic 500 determines whether the sampled voltage $V_{CAP}$ is greater than the nominal battery voltage $V_{BATT\_NOM}$, e.g., $V_{CAP}<V_{BAT\_NOM}$, for more than half the cycles. When the sampled voltage $V_{CAP}$ is not greater than the nominal battery voltage $V_{BATT\_NOM}$, e.g., $V_{CAP}<V_{BAT\_NOM}$, for more than half the cycles, the logic continues along No branch to 502, where it waits for a new broadcast packet and the process begins anew.

Accordingly, the process 500 determines a predetermined threshold of where the battery 302 should operate. For example, in one example, as long as the battery 302 voltage is about 1V and recovers to about 1V, then the system 300 is likely to operate within design parameters. Decision logic for automatic calibration tune-up and tune-down processes, as described hereinbelow in connection with FIGS. 6 and 7, are employed to change both the current (i) that is delivered by the battery 302 and the pulse width (w) of the broadcast signal 306 to optimize the total charge being delivered by the battery 302.

Figure 6:
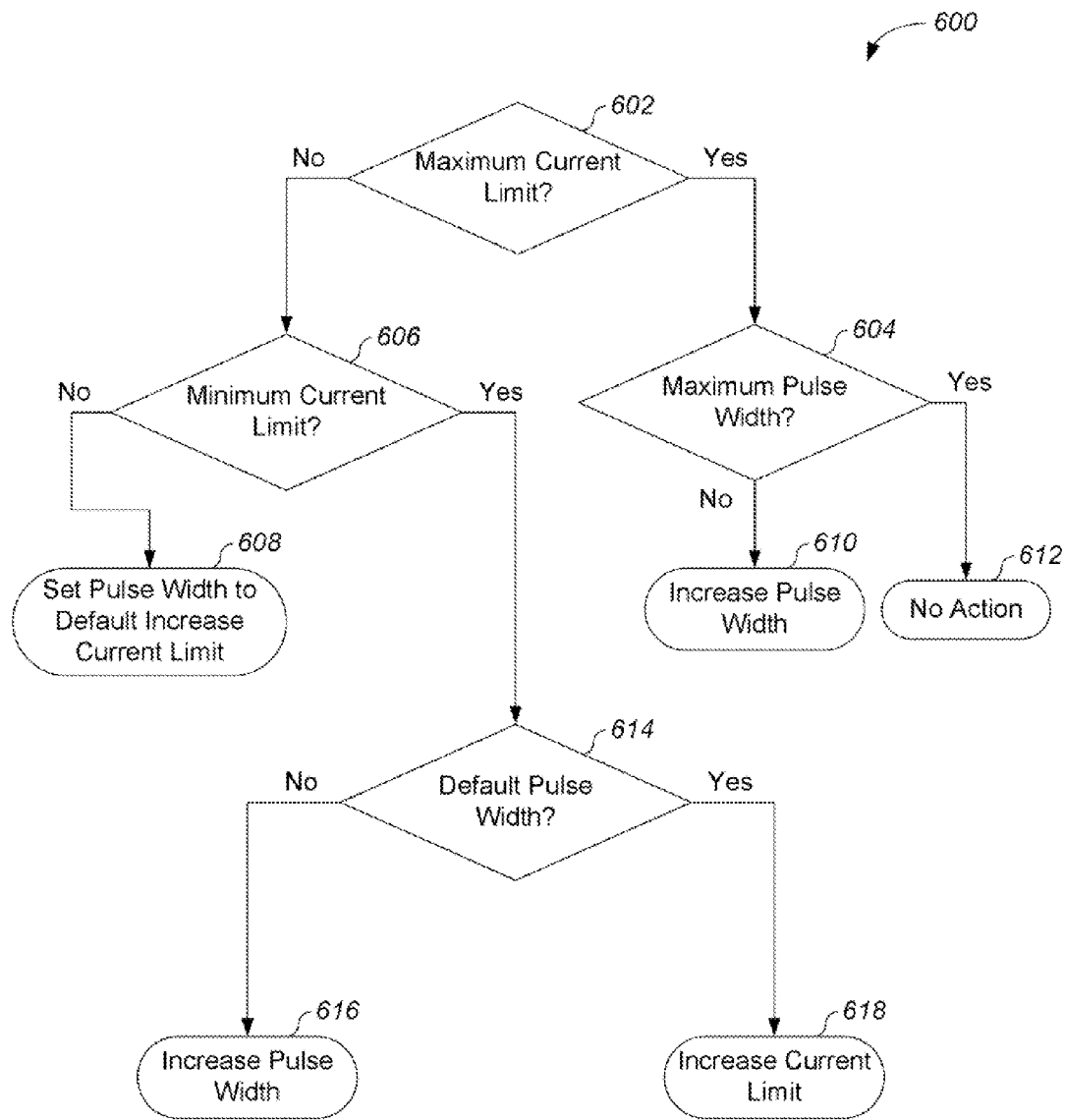
FIG. 6 illustrates one aspect of a decision logic for an automatic calibration tune-up process.

FIG. 6 illustrates one aspect of a decision logic 600 for an automatic calibration tune-up process. In one aspect, the decision logic 600 may be implemented by the circuit 208, for example. When the automatic calibration decision logic 500 process passes to the tune-up decision logic 600 portion of the automatic calibration process, at decision block 602, the decision logic 600 determines whether the battery 302 current (i) is at a maximum current limit ($i_{max}$). When the battery 302 current (i) is at the maximum current limit ($i_{max}$), the logic 600 process continues along Yes branch to decision block 604, where it determines whether a bit of the broadcast signal 306 pulse width (w) is at the maximum pulse width ($w_{max}$). When the pulse width (w) is less than the maximum pulse width ($w_{max}$) ($w<w_{max}$), at 610, the logic 600 process increases the pulse width (w) by a predetermined increment value. In one aspect, the $f_1$ frequency increment value is about 2 µs, and may be selected from the range of about 7.5 µs to about 25 µs, for example. When the pulse width (w) is at the maximum pulse width ($w_{max}$) ($w=w_{max}$), at 612 the logic 600 process takes no action.

When the battery 302 current (i) is not at the maximum current limit ($i_{max}$), the logic 600 process continues along No branch to decision block 606, where it determines whether the battery current (i) is at the minimum current ($i_{min}$) limit, which is predetermined by a value stored in non-volatile memory, for example, about 1 mA. When the battery 302 current (i) is not at the minimum current limit ($i_{min}$), the logic 600 process continues along No branch to 608 to set the pulse width to default to increase current limit. When the battery 302 current (i) is at the minimum current limit ($i_{min}$), the logic 600 process continues along Yes branch to decision block 614 to determine whether the pulse width (w) is set to the default pulse width value. When the pulse width (w) is not set to the default pulse width value, the logic 600 process proceeds along No branch to 616 to increase the pulse width by a predetermined pulse width increment value. In one aspect, the predetermined pulse width increment value is about 2 µs. When the pulse width (w) is set to the default pulse width value, the logic 600 process proceeds along Yes branch to 618 to increase the current (i) limit by a predetermined current increment value. In one aspect, the predetermined current increment value is about 200 µA and may be selected from the range of about 200 µA to about 4 mA, for example.

Figure 7:
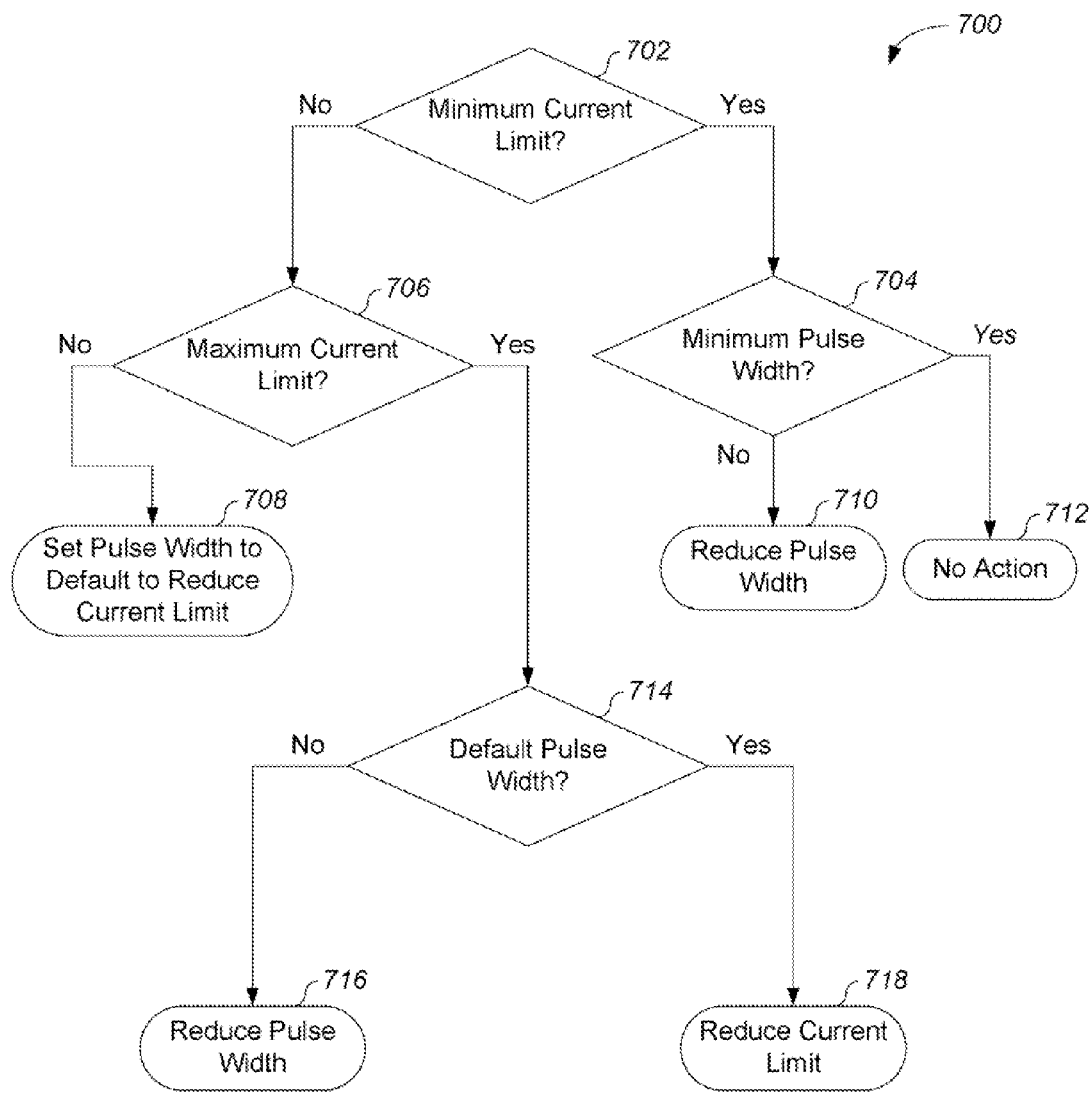
FIG. 7 illustrates one aspect of a decision logic for an automatic calibration tune-down process.

FIG. 7 illustrates one aspect of a decision logic 700 for an automatic calibration tune-down process. In one aspect, the decision logic 700 may be implemented by the circuit 208, for example. When the automatic calibration decision logic 500 process passes to the tune-down decision logic 700 portion of the automatic calibration process, at decision block 702, the decision logic 700 determines whether the battery 302 current (i) is at a minimum current limit ($i_{min}$). When the battery 302 current (i) is at the minimum current limit ($i_{min}$), the logic 700 process continues along Yes branch to decision block 704, where it determines whether a bit of the broadcast signal 306 pulse width (w) is at the minimum pulse width ($w_{min}$). When the pulse width (w) is greater than the minimum pulse width ($w_{max}$) ($w>w_{max}$), at 710, the logic 700 process decreases (reduces) the pulse width (w) by a predetermined decrement value. In one aspect, the $f_1$ frequency decrement value is about 2 µs and may be selected from the range of about 7.5 µs to about 25 μs, for example. When the pulse width (w) is at the minimum pulse width ($w_{min}$) ($w=w_{min}$), at 712 the logic 700 process takes no action.

When the battery 302 current (i) is not at the minimum current limit ($i_{max}$), the logic 700 process continues along No branch to decision block 706 to determine whether the battery current (i) is at the maximum current ($i_{max}$) limit of about 4 mA. When the battery 302 current (i) is not at the maximum current limit ($i_{max}$), the logic 700 process continues along No branch to 708 to set the pulse width to default to reduce the current limit. When the battery 302 current (i) is at the maximum current limit ($i_{max}$), the logic 700 process continues along Yes branch to decision block 714 to determine whether the pulse width (w) is set to the default pulse width value. When the pulse width (w) is not set to the default pulse width value, the logic 700 process proceeds along No branch to 716 to decrease or reduce the pulse width by a predetermined pulse width decrement value. In one aspect, the predetermined pulse width decrement value is about 2 μs and may be selected from the range of about 7.5 μs to about 25 μs, for example. When the pulse width (w) is set to the default pulse width value, the logic 700 process continues along Yes branch to 718 to decrease or reduce the current (i) limit by a predetermined current decrement value. In one aspect, the predetermined current decrement value is about 200 μA and may be selected from the range of about 200 μA to about 4 mA, for example.

Embodiment 2

Figure 8:
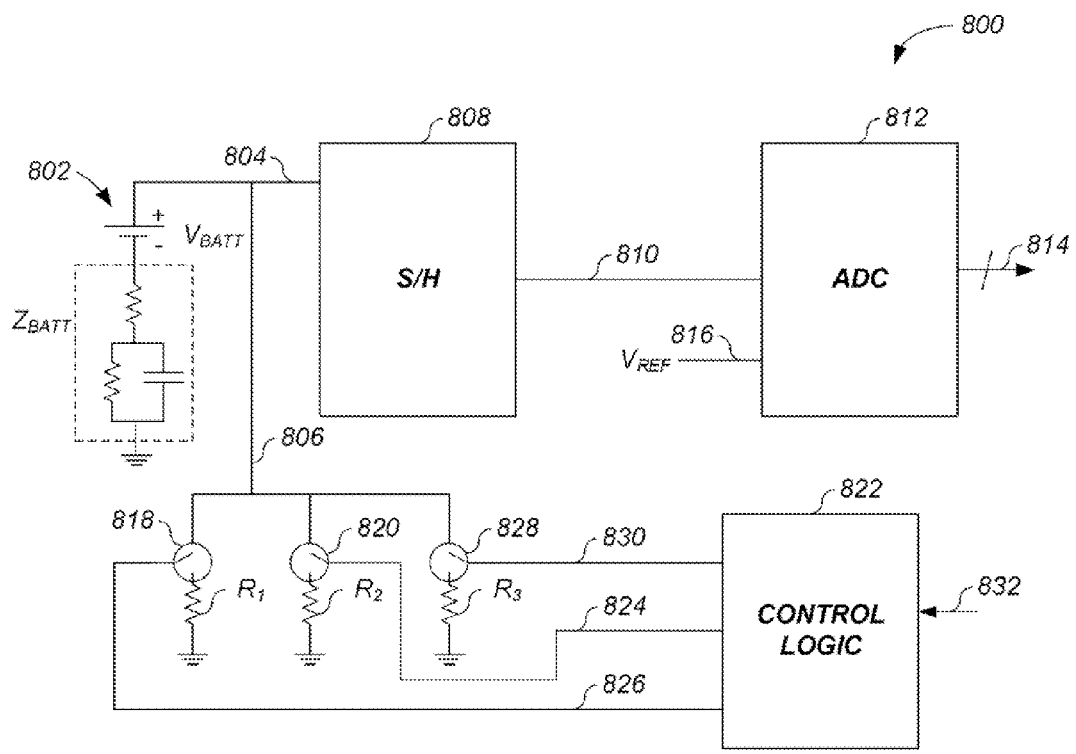
FIG. 8 illustrates one aspect of a battery availability determination circuit to determine the availability of battery power prior to the ingestible communication device entering a high current draw mode of operation.

With reference now to FIG. 8, in another aspect, the present disclosure is directed generally to an apparatus, system, and method to determine the availability of battery power prior to the ingestible communication device entering a high current draw mode of operation. For ingestible device, such as IEM, operations, where the impedance $Z_{BATT}$ of the battery 802 is determined by the amount of material dissolution over time, and could vary by a factor of ten or more, it may be desirable to know that the battery 802 is capable of sustaining a predetermined current draw prior to performing broadcast communication operations. One example of this type of operation is the reading or programming of a non volatile memory, whereby a failure of the reading or writing of that memory would result in non-operation or incorrect operation of the IEM.

In one aspect, a battery availability determination circuit 800 maybe employed to determine the availability of battery power prior to the ingestible communication device entering a high current draw mode of operation. In one aspect, the battery availability determination circuit 800 comprises a power on reset control logic circuit 822 and a low power ADC 812 are used to determine the impedance $Z_{BATT}$ of the battery 802. The power on reset control logic circuit 822 is configured to control the operation of first and second analog switches 818, 820 to connect either a first, second, or third load resistance R1, R2, or R3, respectively, in parallel with the battery 802. A voltage 806 developed across each resistor R1, R2, R3, is coupled into an input 804 of a sample-and-hold (S/H) circuit 808. The output 810 of the S/H circuit 808 is coupled to and measured by the ADC 812. The measured battery voltage ($Vb_{meas}$) output 814 of the ADC 812 is coupled to the logic circuit 208 (FIG. 3) of the communication system 300 (FIG. 3) for calculating the impedance $Z_{BATT}$ of the battery 802 based on two out three of the voltage measurements. A reference voltage 816 ($V_{REF}$) may be provided internal or external to the ADC 812.

The operation of the battery availability determination circuit 800 is as follows. The power on reset control logic circuit 822 receives a power on reset signal 832 and detects a point when the battery 802 has reached a pre-determined voltage and current capacity. At this point in time, the ADC 812 is enabled and performs the following measurements. A first known resistor R1 of typical value is connected from the battery 802 to ground by a first analog switch 818 via control 826 and the battery voltage across the first resistor R1 is measured by the ADC 812 by way of the S/H circuit 808. The measured battery voltage $Vb_{meas1}$ is then provided to the logic circuit 208 (FIG. 3). A typical value for the first known predetermined resistor R1 is about 1.5 kΩ and may be selected from the range of about 1.275 kΩ to about 1.725 kΩ, or 1.5 kΩ±15%, for example.

A second known resistor R2 of high value is connected from the battery 802 to ground by a second analog switch 820 via control 824 and the battery voltage developed across the second resistor R2 is measured by the ADC 812 by way of the S/H circuit 808. The measured battery voltage $Vb_{meas2}$ is then provided to the logic circuit 208 (FIG. 3). A typical value for the second known predetermined resistor R2 is about 15 kΩ and may be selected from the range of about 12.75 kΩ to about 17.25 kΩ, or 15 kΩ±15%, for example.

A third known resistor R3 of low value is connected from the battery 802 to ground by a third analog switch 828 via control 830 and the battery voltage developed across the third resistor R3 is measured by the ADC 812 by way of the S/H circuit 808. The measured battery voltage $Vb_{meas3}$ is then provided to the logic circuit 208 (FIG. 3). A typical value for the third known predetermined resistor R3 is about 1Ω and may be selected from the range of about 0.85Ω to about 1.15Ω, or 1Ω±15%, for example.

The values of the high value resistor R2 and the low value resistor R3 may be chosen such that the resultant voltage across either of the resistors R2, R3 will within the ADC 812 measurement range for the battery 802 impedances $V_{BATT}$ being considered. By using two of the three measured battery voltage, $Vb_{meas1}$ (1.5 kΩ), $Vb_{meas2}$ (15 kΩ), and $Vb_{meas3}$ (1Ω) values, the battery impedance is calculated in accordance with the following formula, which employs $Vb_{meas1}$ and $Vb_{meas2}$, for example.

$$Z_{BATT} = \frac{Vb_{meas1} - Vb_{meas2}}{\frac{VB_{meas2}}{R1} - \frac{VB_{meas1}}{R2}}$$

For $Vb_{meas2}$ and $Vb_{meas3}$, the formula is:

$$Z_{BATT} = \frac{Vb_{meas3} - Vb_{meas2}}{\frac{VB_{meas2}}{R3} - \frac{VB_{meas3}}{R2}}$$

For $Vb_{meas1}$ and $Vb_{meas3}$, the formula is:

$$Z_{BATT} = \frac{Vb_{meas3} - Vb_{meas1}}{\frac{VB_{meas1}}{R3} - \frac{VB_{meas3}}{R1}}$$

When the impedance $Z_{BATT}$ of the battery 802 is within acceptable parameters, the high current operation of the battery 802 is enabled, when the battery impedance $Z_{BATT}$ is outside of this range, however, the communication circuit 300

(FIG. 3) (e.g., the IEM) will return to a sleep state and wake up after a predetermined amount of time, or at another occurrence of the power on reset signal 832.

Embodiment 3

Figure 9:
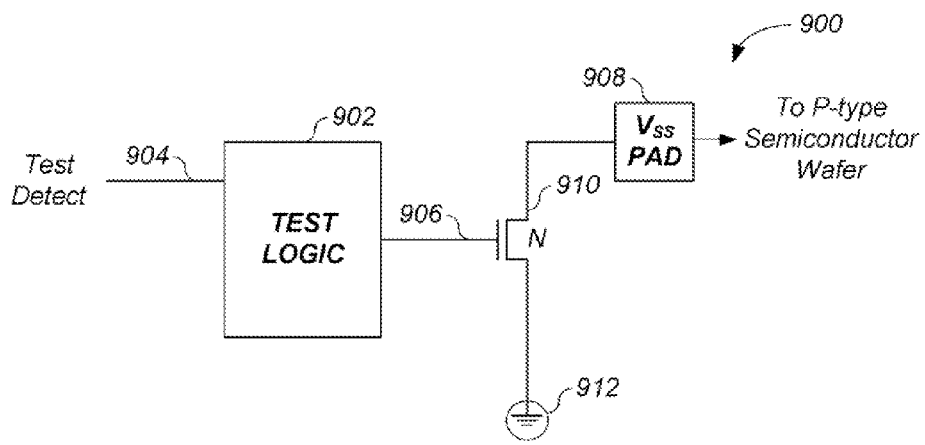
FIG. 9 illustrates a circuit diagram for providing a negative terminal connection that can be placed on the top side of a wafer that is activated only during test modes and is left in a high impedance state during all other modes of operation.

With reference now to FIG. 9, in another aspect, the present disclosure is directed generally to an apparatus, system, and method for integrated circuits using the substrate as a negative terminal. It is not uncommon for complementary metal oxide semiconductor (CMOS) devices using P type starting material to have their substrate referenced to the most negative potential of the system. For an ingestible device, such as IEM, this substrate connection forms the negative terminal of the power source, while the top of the semiconductor wafer is connected to the positive terminal of the power source. Given this configuration, it may difficult to provide a negative terminal connection on the top side of the wafer due to the possibility of either shorting the positive terminal during power source activation, or causing increased leakage currents between the two terminals. This difficulty in providing a negative terminal on the top side of the wafer and relying on the substrate connection only, may cause measurement inaccuracies at wafer sort test due to the impedance from the substrate to the on chip circuits connected to the negative terminal. Accordingly, in one aspect, a negative terminal connection is provided that can be placed on the top side of the wafer that is activated only during test modes and is left in a high impedance state during all other modes of operation.

Accordingly, in one embodiment, FIG. 9 illustrates a circuit diagram 900 for providing a negative terminal connection that can be placed on the top side of a wafer that is activated only during test modes and is left in a high impedance state during all other modes of operation. As illustrated in FIG. 9, a test logic 902 circuit has a test detect input channel and an output channel 906 coupled to the gate terminal of an N-channel field effect transistor device 910. The drain terminal of the N-channel device 910 is coupled to the $V_{SS}$ PAD of a P-channel semiconductor wafer through a probe needle. The source terminal of the N-channel device 910 is coupled to the negative substrate 912 of the semiconductor integrated circuit (IC) and provides an internal connection to the substrate. The IC is first powered with the substrate 912 being the negative terminal. A test mode can be entered by applying the correct voltages and frequency signature to a test enable pin 904 of the test logic 902. Once in the test mode, a signal is activated that enables the N-channel device 901 with a lower ON resistance than the substrate 912 resistance to redirect the current flow through the N-channel device 910 rather than the substrate 912 connection.

Embodiment 4

The present disclosure also is directed generally to an apparatus, system, and method to separate the power source from the broadcast power source in an ingestible device, such as an IEM. In a typical architecture, the power source of an IEM is shared between the digital circuits, analog circuits and I/O circuits. This sharing of the power source results in additional circuitry to: (1) disconnect the shared power source from the analog and digital circuits prior to broadcast as to not affect their operation; (2) store enough charge on storage device so that the analog and digital circuits remain operational during the time the power source is disconnected from these circuits; and (3) connect only to the broadcast circuits; connect the power source to the analog and digital circuits after the broadcast cycle has completed and only when the power source has recovered to a voltage equal to or greater than the potential on the storage device. Accordingly, in one aspect, the present disclosure provides a method whereby the IEM power source can be physically separated into multiple power sources of predetermined values allowing the removal of the charge storage device. In another aspect, the present disclosure provides an architecture to de-sensitize the digital and analog circuits from any coupling effect that the close proximity of one power source to another may cause.

Accordingly, in one aspect the present disclosure describes a method whereby the IEM power source can be physically separated into multiple power sources of predetermined values allowing the removal of the charge storage device. In addition, the present disclosure provides an architecture that is utilized to de-sensitize the digital and analog circuits from any coupling effect that the close proximity of one power source to another may cause.

In one aspect, a method is provided whereby a single IEM power source is divided into multiple smaller power sources. By controlling the area of the positive electrode, it is possible to control the available charge that can be supplied to the circuits connected to that electrode. Further, using a low drop out voltage regulator whose input is connected to one of the power sources and whose output is connected to the analog or digital circuits to be controlled by that power source, and is lower in potential than the power source, any intermittent effects of one power source coupling to another power source can be minimized.

It is also possible to electrically connect and/or disconnect two or more of the power sources to accommodate differing power requirements of the analog and digital circuits. As an example, if one power source has the primary function to power the broadcast circuits, and the second power source has the primary function to power all analog and digital circuits during the broadcast cycle, then one could through a switch, connect both power sources together during non broadcast cycles allowing the analog and digital circuits additional capacity to perform functions that may exceed the capacity of the second power source if used by itself.

Some aspects of the functional modules described in this disclosure may be implemented, for example, using a machine-readable medium or article which may store an instruction or a set of instructions that, if executed by a machine, may cause the machine to perform a method and/or operations in accordance with the aspects. Such a machine may include, for example, any suitable processing platform, computing platform, computing device, processing device, computing system, processing system, computer, processor, or the like, and may be implemented using any suitable combination of hardware and/or software. The machine-readable medium or article may include, for example, any suitable type of memory, memory device, memory article, memory medium, storage device, storage article, storage medium and/or storage unit, for example, memory, removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, universal serial bus (USB) flash drive, various types of Digital Versatile Disk (DVD), a tape, a cassette, or the like. The instructions may include any suitable type of code, such as source code, compiled code, interpreted code, executable code, static code, dynamic code, and the like. The instructions may be implemented using any suitable high-level, low-level, object-oriented, visual, compiled and/or interpreted programming language, such as C, C++, Java, BASIC, Perl, Matlab, Pascal, Visual BASIC, arrangement language, machine code, and so forth.

While various details have been set forth in the foregoing description, it will be appreciated that the various aspects of the apparatus, system, and method to adaptively optimize power dissipation and broadcast power in a power source for a communication device may be practiced without these specific details. For example, for conciseness and clarity selected aspects have been shown in block diagram form rather than in detail. Some portions of the detailed descriptions provided herein may be presented in terms of instructions that operate on data that is stored in a computer memory. Such descriptions and representations are used by those skilled in the art to describe and convey the substance of their work to others skilled in the art. In general, an algorithm refers to a self-consistent sequence of steps leading to a desired result, where a "step" refers to a manipulation of physical quantities which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities.

Unless specifically stated otherwise as apparent from the foregoing discussion, it is appreciated that, throughout the foregoing description, discussions using terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

It is worthy to note that any reference to "one aspect," "an aspect," "one embodiment," or "an embodiment" means that a particular feature, structure, or characteristic described in connection with the aspect is included in at least one aspect. Thus, appearances of the phrases "in one aspect," "in an aspect," "in one embodiment," or "in an embodiment" in various places throughout the specification are not necessarily all referring to the same aspect. Furthermore, the particular features, structures or characteristics may be combined in any suitable manner in one or more aspects.

Some aspects may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

Aspects of the invention are also defined in the following clauses.

Clause 1. A method of stabilizing battery voltage of a battery device while optimizing power delivered to a receiver during communication of a broadcast packet, the method comprising:

receiving, by a logic circuit, a broadcast packet having a predetermined number of bits for communication by a controller to a receiver located remotely from the controller;

determining, by the logic circuit, a number of cycles in which a sampled battery voltage is either greater than or less than or equal to a nominal battery voltage over a first subset of the predetermined number of bits of the broadcast packet; and performing a either a tune-up or tune-down procedure based on the number of cycles counted in which the sampled battery voltage is not equal to the nominal battery voltage for more than one half of a total number of cycles counted.

Clause 2. The method of clause 1, comprising:

performing a tune-up procedure when the sampled battery voltage is greater than the nominal battery voltage for more than one half of a total number of cycles counted; and performing a tune-down procedure when the sampled battery voltage is not greater than the nominal battery voltage for more than one half of a total number of cycles counted.

Clause 3: The method of clause 1 or 2, comprising determining, by the logic circuit, an operating mode, wherein the operating mode is either an X-bit multiple cycle operating mode or a Y-bit single cycle operating mode when the number of cycles in which the sampled battery voltage is not less than the nominal battery voltage for more than one half of a total number of cycles counted.

Clause 4: The method of clause 3, comprising determining, by the logic circuit, the number of cycles over a second subset of the predetermined number of bits of the broadcast packet in which the sampled battery voltage is greater than the nominal battery voltage.

Clause 5: Method of clause 4, comprising determining, by the logic circuit, whether the sampled battery voltage is greater than the nominal battery voltage for more than one half of the cycles over the second subset of the predetermined number of bits of the broadcast packet; preferably further comprising:

waiting, by the logic circuit, for a subsequent broadcast packet when the sampled battery voltage is not greater than the nominal battery voltage for more than one half of the cycles over the second subset of the predetermined number of bits of the broadcast packet; and performing the tune-up procedure when the number of cycles in which the sampled battery voltage is greater than the nominal battery voltage for more than one half of the cycles over the second subset of the predetermined number of bits of the broadcast packet.

Clause 6: The method of any of the preceding clauses, comprising determining, by the logic circuit, the number of cycles over a third subset of the predetermined number of bits of the broadcast packet in which the sampled battery voltage is greater than the nominal battery voltage, preferably comprising determining, by the logic circuit, whether the sampled battery voltage is greater than the nominal battery voltage for more than one half of the cycles over the third subset of the predetermined number of bits of the broadcast packet, the method preferably comprising:

waiting, by the logic circuit, for a subsequent broadcast packet when the sampled battery voltage is not greater than the nominal battery voltage for more than one half of the cycles over the third subset of the predetermined number of bits of the broadcast packet; and performing the tune-up procedure when the number of cycles in which the sampled battery voltage is greater than the nominal battery voltage for more than one half of the cycles over the third subset of the predetermined number of bits of the broadcast packet.

Clause 7: The method of any of the preceding clauses, wherein the tune-up procedure, comprises:
  determining, by a logic circuit, whether a battery current as defined by a predetermined programmable value is at a maximum current limit;
  determining, by the logic circuit, whether the battery current is at a minimum current limit when the battery current is less than the maximum current limit;
  determining, by the logic circuit, whether a bit of the broadcast packet has a default pulse width when the battery current is at the minimum current limit; and
  increasing the pulse width when the pulse width is not at the default pulse width; and
  increasing the current limit when the pulse width is at the default pulse width, preferably comprising setting, by the logic circuit, the pulse width to the default pulse width when the battery current is not at the minimum current limit and/or comprising:
  determining, by the logic circuit, whether the pulse width is at a maximum pulse width when the battery current is at the maximum current limit; and
  increasing, by the logic circuit, the pulse width when the pulse width is not at a maximum pulse width.

Clause 8: The method of clause 7, comprising setting, by the logic circuit, the pulse width to the default pulse width when the battery current is not at the minimum current limit and/or:
  determining, by the logic circuit, whether the pulse width is at a maximum pulse width when the battery current is at the maximum current limit; and
  increasing, by the logic circuit, the pulse width when the pulse width is not at a maximum pulse width.

Clause 9: The method of any of the preceding clauses, wherein the tune-down procedure, comprises:
  determining, by a logic circuit, whether a battery current is at a minimum current limit;
  determining, by the logic circuit, whether the battery current is at a maximum current limit when the battery current is less than the minimum current limit;
  determining, by the logic circuit, whether a bit of the broadcast packet has a default pulse width when the battery current is at the maximum current limit; and
  decreasing the pulse width when the pulse width is not at the default pulse width; and
  decreasing the current limit when the pulse width is at the default pulse width.

Clause 10: The method of clause 9, comprising setting, by the logic circuit, the pulse width to the default pulse width when the battery current is not at the maximum current limit and/or determining, by the logic circuit, whether the pulse width is at a minimum pulse width when the battery current is at the minimum current limit; and reducing, by the logic circuit, the pulse width when the pulse width is not at a minimum pulse width.

Clause 11: A logic circuit configured to stabilize battery voltage of a battery device while optimizing power delivered to a receiver during communication of a broadcast packet, the logic circuit comprising a processor configured to:
  receive a broadcast packet having a predetermined number of bits for communication to a receiver located remotely from the controller;
  determine a number of cycles in which a sampled battery voltage is either greater than or less than or equal to a nominal battery voltage over a first subset of the predetermined number of bits of the broadcast packet; and
  perform a either a tune-up or tune-down procedure based on the number of cycles counted in which the sampled battery voltage is not equal to the nominal battery voltage for more than one half of a total number of cycles counted.

Clause 12: The logic circuit of clause 11, comprising:
  a sample-and-hold circuit; and
  an analog-to-digital converter, each coupled to the processor and the battery;
  wherein the analog-to-digital converter samples the battery voltage to determine the sampled battery voltage,
  wherein the logic circuit preferably comprises a battery coupled to the processor.

Clause 13: The logic circuit of clause 11 or 12, wherein the logic circuit is configured to perform the method as defined in any of clauses 1-10.

Clause 14: A communication system comprising a logic circuit according to any of clauses 11-13, wherein the battery device is an event indicator system,
  the event indicator system comprising dissimilar metals positioned on opposite ends, wherein the event indicator is configured to generate a voltage potential when the dissimilar metals positioned on opposite ends dissolve in a conducting fluid.

Clause 15: The communication system of clause 14, comprising:
  a sample-and-hold circuit; and
  an analog-to-digital converter, each coupled to the processor and the event indicator;
  wherein the analog-to-digital converter is to sample the voltage potential to determine the sampled battery potential.

While certain features of the aspects have been illustrated as described herein, many modifications, substitutions, changes and equivalents will now occur to those skilled in the art. It is therefore to be understood that the appended claims are intended to cover all such modifications and changes as fall within the true spirit of the aspects.

The invention claimed is:

1. A method of stabilizing battery voltage of a battery device while optimizing power delivered to a receiver during communication of a broadcast packet, the method comprising:
  receiving, by a logic circuit, a broadcast packet having a predetermined number of bits for communication by a controller to a receiver located remotely from the controller;
  determining, by the logic circuit, a number of cycles in which a sampled battery voltage is either greater than or less than or equal to a nominal battery voltage over a first subset of the predetermined number of bits of the broadcast packet; and
  performing a either a tune-up or tune-down procedure based on the number of cycles counted in which the sampled battery voltage is not equal to the nominal battery voltage for more than one half of a total number of cycles counted.

2. The method of claim 1, comprising:
  performing a tune-up procedure when the sampled battery voltage is greater than the nominal battery voltage for more than one half of a total number of cycles counted; and
  performing a tune-down procedure when the sampled battery voltage is not greater than the nominal battery voltage for more than one half of a total number of cycles counted.

3. The method of claim 1, comprising determining, by the logic circuit, an operating mode, wherein the operating mode is either an X-bit multiple cycle operating mode or a Y-bit single cycle operating mode when the number of cycles in which the sampled battery voltage is not less than the nominal battery voltage for more than one half of a total number of cycles counted.

4. The method of claim 3, comprising determining, by the logic circuit, the number of cycles over a second subset of the predetermined number of bits of the broadcast packet in which the sampled battery voltage is greater than the nominal battery voltage.

5. The method of claim 4, comprising determining, by the logic circuit, whether the sampled battery voltage is greater than the nominal battery voltage for more than one half of the cycles over the second subset of the predetermined number of bits of the broadcast packet.

6. The method of claim 5, comprising:
waiting, by the logic circuit, for a subsequent broadcast packet when the sampled battery voltage is not greater than the nominal battery voltage for more than one half of the cycles over the second subset of the predetermined number of bits of the broadcast packet; and
performing the tune-up procedure when the number of cycles in which the sampled battery voltage is greater than the nominal battery voltage for more than one half of the cycles over the second subset of the predetermined number of bits of the broadcast packet.

7. The method of claim 3, comprising determining, by the logic circuit, the number of cycles over a third subset of the predetermined number of bits of the broadcast packet in which the sampled battery voltage is greater than the nominal battery voltage.

8. The method of claim 7, comprising determining, by the logic circuit, whether the sampled battery voltage is greater than the nominal battery voltage for more than one half of the cycles over the third subset of the predetermined number of bits of the broadcast packet.

9. The method of claim 8, comprising:
waiting, by the logic circuit, for a subsequent broadcast packet when the sampled battery voltage is not greater than the nominal battery voltage for more than one half of the cycles over the third subset of the predetermined number of bits of the broadcast packet; and
performing the tune-up procedure when the number of cycles in which the sampled battery voltage is greater than the nominal battery voltage for more than one half of the cycles over the third subset of the predetermined number of bits of the broadcast packet.

10. The method of claim 1, wherein the tune-up procedure, comprises:
determining, by a logic circuit, whether a battery current as defined by a predetermined programmable value is at a maximum current limit;
determining, by the logic circuit, whether the battery current is at a minimum current limit when the battery current is less than the maximum current limit;
determining, by the logic circuit, whether a bit of the broadcast packet has a default pulse width when the battery current is at the minimum current limit; and
increasing the pulse width when the pulse width is not at the default pulse width; and
increasing the current limit when the pulse width is at the default pulse width.

11. The method of claim 10, comprising setting, by the logic circuit, the pulse width to the default pulse width when the battery current is not at the minimum current limit.

12. The method of claim 10, comprising:
determining, by the logic circuit, whether the pulse width is at a maximum pulse width when the battery current is at the maximum current limit; and
increasing, by the logic circuit, the pulse width when the pulse width is not at a maximum pulse width.

13. The method of claim 1, wherein the tune-down procedure, comprises:
determining, by a logic circuit, whether a battery current is at a minimum current limit;
determining, by the logic circuit, whether the battery current is at a maximum current limit when the battery current is less than the minimum current limit;
determining, by the logic circuit, whether a bit of the broadcast packet has a default pulse width when the battery current is at the maximum current limit; and
decreasing the pulse width when the pulse width is not at the default pulse width; and
decreasing the current limit when the pulse width is at the default pulse width.

14. The method of claim 13, comprising setting, by the logic circuit, the pulse width to the default pulse width when the battery current is not at the maximum current limit.

15. The method of claim 13, comprising:
determining, by the logic circuit, whether the pulse width is at a minimum pulse width when the battery current is at the minimum current limit; and
reducing, by the logic circuit, the pulse width when the pulse width is not at a minimum pulse width.

16. A logic circuit configured to stabilize battery voltage of a battery device while optimizing power delivered to a receiver during communication of a broadcast packet, the logic circuit comprising:
a processor configured to receive a broadcast packet having a predetermined number of bits for communication by a controller to a receiver located remotely from the controller;
determine a number of cycles in which a sampled battery voltage is either greater than or less than or equal to a nominal battery voltage over a first subset of the predetermined number of bits of the broadcast packet; and
perform a either a tune-up or tune-down procedure based on the number of cycles counted in which the sampled battery voltage is not equal to the nominal battery voltage for more than one half of a total number of cycles counted.

17. The logic circuit of claim 16, comprising:
a sample-and-hold circuit; and
an analog-to-digital converter, each coupled to the processor and the battery;
wherein the analog-to-digital converter samples the battery voltage to determine the sampled battery voltage.

18. The logic circuit of claim 17, comprising a battery coupled to the processor.

19. A communication system, comprising:
a processor configured to stabilize a voltage potential generated by an event indicator while optimizing power delivered to a receiver during communication of a broadcast packet by the event indicator to the receiver, the broadcast packet having a predetermined number of bits; and
an event indicator system with dissimilar metals positioned on opposite ends, wherein the event indicator is configured to generate a voltage potential when the dissimilar metals positioned on opposite ends dissolve in a conducting fluid;
wherein the processor is further configured to:
determine a number of cycles in which a sampled voltage potential is either greater than or less than or equal to a nominal voltage potential over a first subset of the predetermined number of bits of the broadcast packet;

perform a either a tune-up or tune-down procedure based on the number of cycles counted in which the sampled battery voltage is not equal to the nominal battery voltage for more than one half of a total number of cycles counted.

20. The communication system of claim 19, comprising:
a sample-and-hold circuit; and
an analog-to-digital converter, each coupled to the processor and the event indicator;
wherein the analog-to-digital converter is to sample the voltage potential to determine the sampled battery potential.

* * * * *